(12) United States Patent
Schweinsberg

(10) Patent No.: US 9,161,897 B2
(45) Date of Patent: *Oct. 20, 2015

(54) COMPOSITIONS FOR COLOURING KERATINOUS FIBRES

(71) Applicant: Henkel AG & Co. KGaA, Düsseldorf (DE)

(72) Inventor: Matthias Schweinsberg, Hamburg (DE)

(73) Assignee: HENKEL AG & CO. KGAA, Duesseldorf (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/308,594

(22) Filed: Jun. 18, 2014

(65) Prior Publication Data

US 2014/0298599 A1 Oct. 9, 2014

Related U.S. Application Data

(63) Continuation of application No. PCT/EP2012/072350, filed on Nov. 12, 2012.

(30) Foreign Application Priority Data

| Dec. 13, 2011 | (DE) | 10 2011 088 397 |
| Dec. 13, 2011 | (DE) | 10 2011 088 398 |
| Dec. 19, 2011 | (DE) | 10 2011 089 060 |
| Dec. 19, 2011 | (DE) | 10 2011 089 063 |

(51) Int. Cl.
*A61Q 5/10* (2006.01)
*A61K 8/72* (2006.01)
*A61K 8/58* (2006.01)
*A61K 8/893* (2006.01)

(52) U.S. Cl.
CPC . *A61K 8/72* (2013.01); *A61K 8/585* (2013.01); *A61K 8/893* (2013.01); *A61Q 5/10* (2013.01); *A61K 2800/544* (2013.01)

(58) Field of Classification Search
CPC ............ A61Q 5/10; A61Q 5/04; A61K 8/86; A61K 8/893
USPC ................. 424/70.1, 70.122; 8/405
See application file for complete search history.

(56) References Cited

U.S. PATENT DOCUMENTS

2004/0163187 A1* 8/2004 Cottard et al. ............... 8/405
2012/0260934 A1* 10/2012 Schweinsberg et al. ...... 132/203

FOREIGN PATENT DOCUMENTS

| EP | 998908 | 5/2000 |
| EP | 2168633 A2 | 3/2010 |
| EP | 2266582 A1 | 12/2010 |
| WO | 2009024450 A1 | 2/2009 |
| WO | 2011015512 | 2/2011 |
| WO | 2011015513 | 2/2011 |
| WO | 2011015514 | 2/2011 |
| WO | WO 2011/080034 A1 * | 7/2011 ............... A61Q 5/00 |

OTHER PUBLICATIONS

STIC Search Report dated Oct. 7, 2014.*

* cited by examiner

*Primary Examiner* — Eisa Elhilo
(74) *Attorney, Agent, or Firm* — Steven L. Nichols; Van Cott, Bagley, Cornwall & McCarthy P.C.

(57) ABSTRACT

An active agent combination of (a) at least one water-soluble polymer comprising at least one *—Si(OR)$_x$(R')$_{3-x}$ residue, in which R and R', independently of one another, denote a (C$_1$ to C$_4$)alkyl group, and x denotes 1, 2 or 3, and (b) at least one polar alkoxysilane compound of formula (SI), in which G denotes a (C$_1$ to C$_3$)alkylene group, K" denotes a connectivity selected from a covalent bond or from a molecular fragment having two free valences, R$^1$ denotes a molecular fragment comprising at least one polar substituent selected from the group consisting of quaternized nitrogen atoms, amino groups, anionic residues, and combinations thereof, x denotes 1, 2 or 3, R and R', independently of one another, denote a (C$_1$ to C$_4$)alkyl group, is suitable for improving synthetic colorings of coloring compounds on keratin-containing fibers.

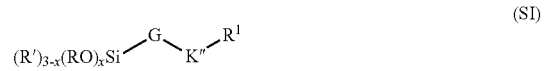

(SI)

20 Claims, No Drawings

COMPOSITIONS FOR COLOURING KERATINOUS FIBRES

RELATED DOCUMENTS

The present application claims the benefit and is a U.S. continuation patent application under 35 U.S.C. 111(a) and claims the right of priority under 35 U.S.C. 365 to international patent Application No. PCT/EP2012/072350, filed Nov. 12, 2012, entitled "Compositions for Colouring Keratinous Fibres" which claims benefit of German application No.: 102011089060.2, filed Dec. 19, 2011, these applications are herein incorporated by reference in their entirety.

FIELD OF THE INVENTION

The present application relates generally to cosmetic agents for coloring keratin-containing fibers. More specifically, the present application relates to an agent for coloring keratin-containing fibers that includes water-soluble polymer and a polar alkoxysilane.

BACKGROUND OF THE INVENTION

Various systems provide cosmetic agents for coloring, in particular for keratin-containing fibers, such as human hair. The selection of such a system depends on the requirements of the coloring process.

Oxidation coloring agents are used for permanent, intense colors with corresponding fastness properties. Such coloring agents conventionally include oxidation dye precursors known as "developer components" and "coupler components." Under the influence of oxidizing agents, or of atmospheric oxygen, the developer components form the actual dyes with one another or by coupling with one or more coupler components. Oxidation coloring agents are characterized by outstanding, long-lasting coloring results. In order to achieve natural-looking colors, however, a mixture of a relatively large number of oxidation dye precursors usually has to be used; in many cases substantive dyes are also used for shading.

Primary aromatic amines having a further free or substituted hydroxyl or amino group in para- or ortho-position, heterocyclic hydrazones, diaminopyrazole derivatives and 2,4,5,6-tetraaminopyrimidine and derivatives thereof may be used as developer components. m-Phenylenediamine derivatives, naphthols, pyridine derivatives, resorcinol and resorcinol derivatives, pyrazolones and m-aminophenols may be used as coupler components.

For temporary colors, coloring or tinting agents may be used; these agents include substantive dyes as the coloring component. Substantive dyes are dye molecules which attach directly to the substrate and require no oxidative process to develop the color. These colors may be significantly more sensitive to shampooing than oxidative colors, such that an often undesired shift in shade, or a visible homogeneous color loss, occurs much more quickly.

Finally, another coloring method has attracted great attention. In this method, precursors of the natural hair dye melanin are applied to the substrate, for example hair. Through oxidative processes these melanin precursors then develop nature-analogous dyes in the hair. It is possible to restore the natural hair color of people with gray hair with repeated use in particular of agents including 5,6-dihydroxyindoline. Pigment removal may be carried out using atmospheric oxygen as the sole oxidizing agent, avoiding the need to use a further oxidizing agent. For people whose original hair color is medium blond to brown, indoline may be used as the sole dye precursor. By contrast, for people whose original hair color is red, and in particular darker to black, satisfactory results may frequently only be obtained with the additional use of further dye components, in particular special oxidation dye precursors.

One consequence of an improvement in color intensity or coloring power for example of the dyes used is that expensive dyes may be used more economically. The colors obtained should moreover have a high degree of color fastness, with respect to harsh treatments such as sweat, washing, light or friction for example. Additionally, in the context of hair care in particular, products should be compatible with the use of other hair treatment agents. A uniform color along the keratin-containing fibers is likewise a requirement of a commercially successful coloring agent for keratin-containing fibers. As natural products, keratinic fibers, such as human hair, have uneven structural properties along the fiber. For example, the keratin-containing material of the fiber at the tip and along the length of the hair has been exposed to environmental influences for a longer time than the regions of the fiber in the vicinity of the hair root and therefore exhibits greater deviation from the original natural fiber structure. Differences in the fiber structure often lead to an uneven color uptake and to an uneven fading of the color due to environmental influences. The color is visually perceived as uneven.

Consequently, an object of the present specification is therefore to provide a cosmetic composition for coloring keratin-containing fibers which brings about an improved color and does not present the above disadvantages.

Document WO-A1-2009/024450 describes star-shaped polyether-containing compounds which may be used in agents for cleaning surfaces and which inhibit resoiling of the cleaned substrate.

Documents WO-A1-2011/015512, WO-A1-2011/015513 and WO-A1-2011/015514 propose alkoxysilylated, polyether-containing compounds for use on the hair.

Improving the color fastness of synthetic colorings on keratin-containing fibers with alkoxysilylated, polyether-containing compounds is not known in the industry.

Furthermore, other desirable features and characteristics of the present invention will become apparent from the subsequent detailed description of the invention and the appended claims, taken in conjunction with this background of the invention.

BRIEF SUMMARY OF THE INVENTION

The present specification therefore provides a method to improve synthetic colorings of coloring compounds on keratin-containing fibers, wherein the method includes applying an active agent combination. The active agent combination includes (a) at least one water-soluble polymer comprising at least one *—Si(OR)$_x$(R')$_{3-x}$ residue, in which R and R', independently of one another, denote a (C$_1$ to C$_4$)alkyl group and x denotes 1, 2 or 3, and (b) at least one polar alkoxysilane compound of formula (SI)

in which G denotes a (C$_1$ to C$_3$)alkylene group, K" denotes a connectivity selected from a covalent bond or from a molecular fragment having two free valences, R$^1$ denotes a molecular fragment including at least one polar substituent selected from the group consisting of quaternized nitrogen atoms, amino groups, anionic residues, or combinations thereof, x denotes 1, 2 or 3, and R and R', independently of one another, denote a ($C_1$ to $C_4$)alkyl group.

The present specification also provides a cosmetic agent for coloring keratin-containing fibers. The cosmetic agent includes, in a cosmetic carrier: (a) at least one water-soluble polymer comprising at least one *—Si(OR)$_x$(R')$_{3-x}$ residue, in which R and R', independently of one another, denote a ($C_1$ to $C_4$)alkyl group and x denotes 1, 2 or 3, and (b) at least one polar alkoxysilane compound of formula (SI),

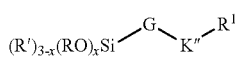
(SI)

in which G denotes a ($C_1$ to $C_3$)alkylene group, K" denotes a connectivity selected from a covalent bond or from a molecular fragment having two free valences, $R^1$ denotes a molecular fragment comprising at least one polar substituent selected from the group consisting of quaternized nitrogen atoms, amino groups, anionc residues, or combinations thereof, x denotes 1, 2 or 3, and R and R', independently of one another, denote a ($C_1$ to $C_4$)alkyl group.

DETAILED DESCRIPTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The use of an active agent combination on previously colored keratin-containing fibers (in particular during the coloring process) improves the color fastness of the color, in particular the wash fastness of the color. Repeated washing of the fibers does not cause uneven coloring along the keratinic fiber from the root to the tips as a result of the color washing out unevenly. The color maintains good equalization.

According to the present specification the term "keratin-containing fibers," "keratin fibers," or similar terminology is understood to mean fur, wool, feathers and in particular human hair.

The coloring compounds within the meaning of the present specification are preferably selected from:
(1) at least one oxidation dye precursor of the developer component type and optionally additionally at least one coupler component
and/or
(2) at least one substantive dye
and/or
(3) at least one precursor of nature-analogous dyes.

Particularly preferred coloring compounds are selected from at least one oxidation dye precursor of the developer component type and optionally additionally at least one coupler component.

Preferred representatives of the coloring compounds from (1), (2) and (3) (see above) are defined in the second subject matter of the present specification (see below).

An active agent combination includes components (a) and (b). Preferred representatives of components (a) and (b) of said active agent combination (see Brief Description of the Invention) are defined in the second subject matter of the present specification (see below).

The cosmetic use of the present specification is improved by incorporating said active agent combination into a cosmetic carrier. The cosmetic agents for coloring keratin-containing fibers of the present specification, as specified below, are therefore preferably used.

The present specification provides a cosmetic agent for coloring keratin-containing fibers, in particular human hair, including in a cosmetic carrier,
(a) at least one water-soluble polymer comprising at least one *—Si(OR)$_x$(R')$_{3-x}$ residue, in which R and R', independently of one another, denote a ($C_1$ to $C_4$)alkyl group (in particular methyl or ethyl), x denotes 1, 2 or 3,
and
(b) at least one polar alkoxysilane compound of formula (SI)

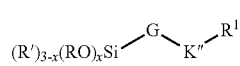
(SI)

in which:
G denotes a ($C_1$ to $C_3$)alkylene group,
K" denotes a connectivity selected from a covalent bond or from a molecular fragment having two free valences,
$R^1$ denotes a molecular fragment comprising at least one polar substituent selected from at least one representative of the group formed from
quaternized nitrogen atoms
amino groups
anionic residues
x denotes 1, 2 or 3,
R and R' independently of one another, denote a ($C_1$ to $C_4$)alkyl group (in particular methyl or ethyl),
and
(c) at least one coloring compound.

Preferred cosmetic carriers are aqueous cosmetic carriers, alcoholic cosmetic carriers or aqueous-alcoholic cosmetic carriers. For the purposes of coloring keratin-containing fibers, such carriers are for example lotions, water-in-oil emulsions, oil-in-water emulsions, creams, gels, foams or other preparations that are suitable for use on the hair.

Within the meaning of the present specification aqueous-alcoholic carriers are understood to be aqueous compositions including 3 to 70 weight percent (wt. %) of an organic solvent, in particular a $C_1$-$C_7$ alcohol (preferably ethanol, isopropanol, glycerol, benzyl alcohol, ethyl diglycol, 1,2-propylene glycol or 1,3-propylene glycol, methoxybutanol). All water-soluble organic solvents are preferred for use in the present specification.

The polar alkoxysilane compounds of component (b) are different from said water-soluble polymers of component (a).

If a chemical bond in a structural formula is marked with the symbol *, it denotes a free valence of the corresponding structural fragment.

Polymers are understood according to the present specification to be chemical compounds having a molecular weight of at least 5000 grams per mole (g/mol). Polymers are synthesized from a large number of molecules, in which one type or a plurality of types of atoms or atom groupings (known as constitutive units, basic building blocks, monomers, or repeat units) are arranged next to one another in repeating series. The polymers are obtained by a polymerization reaction, which may take place artificially (i.e. synthetically) or naturally.

Within the meaning of the present specification, chemical compounds (e.g. polymers) are said to be "water-soluble" if 0.5 grams (g) or more of the chemical compound dissolves in 100 g water at pH 8 and at 20 degrees Celsius (° C.).

Substituents of the group that is formed from quaternized nitrogen atoms, amino groups and anionic residues are polar within the meaning of the present specification.

Said water-soluble polymers are preferably included in the agents according to the present specification in an amount of from 0.01 to 15.0 wt. %, particularly preferably from 0.1 to 8.0 wt. %, most particularly preferably from 0.2 to 5.0 wt. %, and most preferably from 0.25 to 2.5 wt. %, relative in each case to the total weight of the agent.

It is likewise preferable according to the present specification for said water-soluble polymers of component (a) and the polar alkoxysilanes of component (b) to be used in the agents according to the present specification in a weight ratio range from 10 to 1 to 1 to 10, preferably from 4 to 1 to 1 to 4, particularly preferably from 1 to 1 to 1 to 2.

For use as the preferred water-soluble polymer (as described above), non-limiting examples include at least one water-soluble, polyether-modified, organic polymer having at least one polyether structural unit is suitable, wherein said structural unit
(i) includes a polyoxyalkylene chain consisting of ethylene oxide units or both ethylene oxide and propylene oxide units, wherein the polyoxyalkylene chain has a maximum proportion of 50 wt. % of propylene oxide units, relative to the weight of the polyoxyalkylene chain, and
(ii) has at least one *—Si(OR)$_x$(R')$_{3-x}$ residue, in which R and R', independently of one another, denote a ($C_1$ to $C_4$)alkyl group (in particular methyl or ethyl), x denotes 1, 2 or 3.

"Polyether structural unit" is understood to be a chemical structural fragment that includes a polyoxyalkylene chain consisting of either ethylene oxide units or both ethylene oxide and propylene oxide units, having a maximum proportion of 50 wt. % of propylene oxide units, relative to the weight of the polyoxyalkylene chain.

The polyether structural unit is optionally covalently bonded to a skeletal molecule either directly or optionally through a chemical bond with a mediating structural fragment. Organic compounds or inorganic metal oxides preferably serve as skeletal molecules in this case. The first group forms a polyether-modified organic compound including the polyether structural unit(s). The second group forms a polyether-modified solid particle including the polyether structural unit(s).

"Organic compounds" are understood to be chemical compounds based on a hydrocarbon structural fragment. Corresponding hydrocarbon structural fragments are derived from linear, branched, cyclic or heterocyclic hydrocarbons, all of which may each be saturated, unsaturated or aromatic.

"Polyether-modified organic compounds" are understood according to the present specification to be organic compounds that are modified with at least one polyether structural unit, the polyether structural unit in each case forming a chemical bond with the organic compound to be modified.

"Solid particle" is understood to mean any solid that is in particulate form at room temperature.

"Polyether-modified solid particles" are understood according to the present specification to be solid particles which are surface-modified with polyethers, wherein the polyethers include a polyoxyalkylene chain consisting of either ethylene oxide units or both ethylene oxide and propylene oxide units, wherein the polyoxyalkylene chain has a maximum proportion of 50 wt. % of propylene oxide units, relative to the weight of the polyoxyalkylene chain.

Within the meaning of the present specification an ethylene oxide unit is understood to be a unit of general formula (1):

$$*-CH_2-CH_2-O-* \qquad \text{Formula (1)}$$

and within the meaning of the present specification a propylene oxide unit is understood to be a unit of general formula (2):

$$*-CH_2-CH(CH_3)-O-* \qquad \text{Formula (2)}$$

If the polyoxyalkylene chain of the polyether structural unit includes both ethylene oxide and propylene oxide units, the maximum proportion of propylene oxide units is preferably less than or equal to 50 wt. %, more preferably less than or equal to 40 wt. %, and particularly preferably at most 30 wt. %, relative to the weight of the polyoxyalkylene chain.

Within the context of a particularly preferred example, the water-soluble, polyether-modified, organic polymer having at least one polyether structural unit is selected from one or more polyether-modified organic compounds having at least one polyether structural unit, preferably at least three polyether structural units, wherein these polyether structural units
(i) include a polyoxyalkylene chain consisting of either ethylene oxide units or both ethylene oxide and propylene oxide units, wherein the polyoxyalkylene chain has a maximum proportion of 50 wt. % of propylene oxide units, relative to the weight of the polyoxyalkylene chain, and
(ii) have at least one *—Si(OR)$_x$(R')$_{3-x}$ residue, in which R and R', independently of one another, denote a ($C_1$ to $C_4$)alkyl group (preferably methyl or ethyl), x denotes 1, 2 or 3.

The at least one polyether-modified organic compound is preferably included in the agents according to the present specification in an amount from 0.01 to 15.0 wt. %, particularly preferably from 0.1 to 8.0 wt. %, most particularly preferably 0.2 to 5.0 wt. %, most preferably from 0.25 to 2.5 wt. %, relative in each case to the total weight of the agent.

Said at least one water-soluble, polyether-modified organic compound is preferably selected from at least one compound of general formula (PE-1)

$$[Q \!-\!\!+\!\!(K'-A-K-T)_n \qquad \text{(PE-1)}$$

in which:
A denotes a polyoxyalkylene chain consisting of either ethylene oxide units or both ethylene oxide and propylene oxide units, wherein the polyoxyalkylene chain has a maximum proportion of 50 wt. % of propylene oxide units, relative to the weight of A,
K and K' independently of one another, denote a connectivity selected from a covalent bond or from a molecular fragment having two free valences,
T denotes a residue $$*-Si(OR)_x(R')_{3-x},$$

in which R and R', independently of one another, denote a ($C_1$ to $C_4$)alkyl group (preferably methyl or ethyl), x denotes 1, 2 or 3,
Q denotes an organic structural fragment derived from linear, branched, cyclic or heterocyclic hydrocarbons, all of which may each be saturated, unsaturated or aromatic,
n denotes an integer from 3 to 64 (in particular 3, 4, 5, 6, 7 or 8).

"A" according to formula (PE-1) preferably denotes a structural fragment of formula (A1):

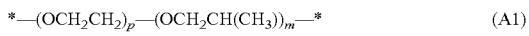 (A1)

in which:
p denotes an integer from 1 to 500,
m denotes an integer from 0 to 500, and
the structural fragment A of formula (A1) has a maximum proportion of 50 wt. % of propylene oxide units, relative to the weight of the structural fragment A of formula (A1). The ethylene oxide and propylene oxide units according to formula (PE-1) or according to formula (A1) may be randomly distributed or distributed as a gradient or may be present in at least two blocks.

If structural fragment A of the compounds according to formula (PE-1) (or according to all subsequent formulae including group A) denotes a polyoxyalkylene chain consisting of ethylene oxide and propylene oxide units, the maximum proportion of propylene oxide units is preferably less than or equal to 50 wt. %, more preferably less than or equal to 40 wt. %, and particularly preferably at most 30 wt. %, relative to the weight of A.

The residues K and K' according to formula (PE-1), preferably (and independently of one another) denote a covalent bond, an oxy group, a ($C_1$ to $C_6$)alkylene group, an imino group or at least one of the following connectivities (K1) to (K10)

 (K1)

 (K2)

 (K3)

 (K4)

 (K5)

 (K6)

 (K7)

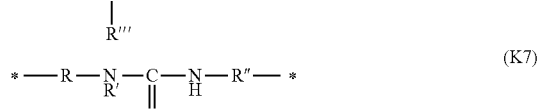 (K8)

 (K9)

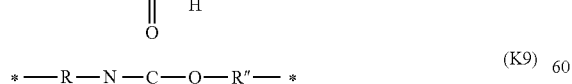 (K10)

in which:
R and R" independently of one another, denote methylene, ethane-1-diyl, propane-1,2-diyl, propane-1,3-diyl, butane-1,2-diyl, butane-1,3-diyl, butane-1,4-diyl or phenylene,
R' denotes a hydrogen atom or a ($C_1$ to $C_4$)alkyl group,
R''' independently of one another, denotes a ($C_1$ to $C_4$)alkyl group or an aryl group.

T according to formula (PE-1) preferably denotes a *—Si(OR)$_x$(R')$_{3-x}$ residue, in which R and R', independently of one another, denote a ($C_1$ to $C_4$)alkyl group (preferably methyl or ethyl) and x denotes 1, 2 or 3. Preferably, T according to formula (PE-1) denotes a triethoxysilyl radical.

The structural fragment —K-T according to formula (PE-1) most particularly preferably denotes a group

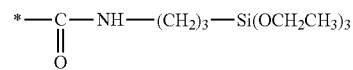

The residue "Q" of formula (PE-1) preferably denotes an organic structural fragment having from 2 to 30 carbon atoms, particularly preferably having from 2 to 20 carbon atoms.)

Q is preferably derived from glycerol, monosaccharide, or disaccharide. Q is most particularly preferably derived from a compound selected from sorbitol, 1,5-anhydrosorbitol, 1,4-anhydrosorbitol, inositol, xylitol, mannitol, gluconolactone, glucuronic acid, 1,2,6-hexanetriol, hydroxyethyl sorbitol, phytantriol, hydroxypropyl phytantriol, lactitol, maltitol, pentaerythritol, polyglycerol-3, glucose, fructose, galactose, ribose, xylose, mannose, sucrose, cellobiose, gentiobiose, isomaltose, lactose, lactulose, maltose, maltulose, melibiose, trehalose, nigerose, palatinose, rutinose, and arabinose.

Most particularly preferred polyether-modified, organic compounds are selected from at least one compound of formula (PE-1a), (PE-1b), (PE-1c), (PE-1d), (PE-1e), (PE-1f) or mixtures thereof,

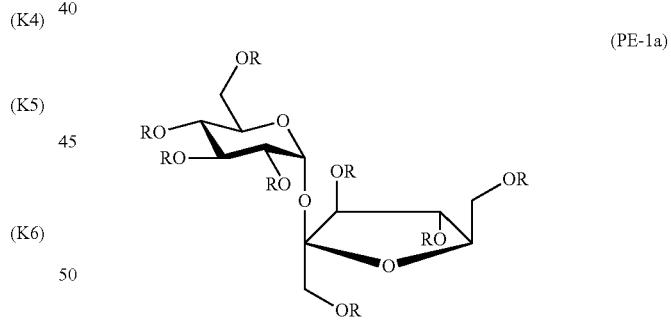 (PE-1a)

in which:
at least three R groups denote a *—(CH$_2$CH$_2$O)$_p$—(CHCH$_3$CH$_2$O)$_m$—K-T group and the other R groups denote a hydrogen atom or a *—K-T group, in which, independently of one another,
p denotes an integer from 1 to 500 and m denotes an integer from 0 to 500, and p and m have a ratio to one another such that there is a maximum proportion of 50 wt. % (preferably a maximum of 40 wt. %, particularly preferably a maximum of 30 wt. %) of propylene oxide units, relative to the weight of the corresponding polyoxyalkylene chain,
K denotes a connectivity selected from a covalent bond or from a molecular fragment having two free valences, T denotes a molecular fragment comprising at least one *—Si(OR)$_x$(R')$_{3-x}$ residue, in which R and R', independently of one another, denote a (C$_1$ to C$_4$)alkyl group (preferably methyl or ethyl), x denotes 1, 2 or 3;

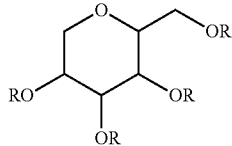

(PE-1b)

in which:

at least three R groups denote a *—(CH$_2$CH$_2$O)$_p$—(CHCH$_3$CH$_2$O)$_m$—K-T group and the other R groups denote a hydrogen atom or a *—K-T group, in which, independently of one another, p denotes an integer from 1 to 500 and m denotes an integer from 0 to 500, and p and m have a ratio to one another such that there is a maximum proportion of 50 wt. % (preferably a maximum of 40 wt. %, particularly preferably a maximum of 30 wt. %) of propylene oxide units, relative to the weight of the corresponding polyoxyalkylene chain, K denotes a connectivity selected from a covalent bond or from a molecular fragment having two free valences, T denotes a molecular fragment comprising at least one *—Si(OR)$_x$(R')$_{3-x}$ residue, in which R and R', independently of one another, denote a (C$_1$ to C$_4$)alkyl group (preferably methyl or ethyl), x denotes 1, 2 or 3;

(PE-1c)

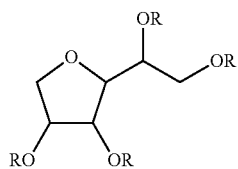

in which:

at least three R groups denote a *—(CH$_2$CH$_2$O)$_p$—(CHCH$_3$CH$_2$O)$_m$—K-T group and the other R groups denote a hydrogen atom or a *—K-T group, in which, independently of one another, p denotes an integer from 1 to 500 and m denotes an integer from 0 to 500, and p and m have a ratio to one another such that there is a maximum proportion of 50 wt. % (preferably a maximum of 40 wt. %, particularly preferably a maximum of 30 wt. %) of propylene oxide units, relative to the weight of the corresponding polyoxyalkylene chain, K denotes a connectivity selected from a covalent bond or from a molecular fragment having two free valences, T denotes a molecular fragment comprising at least one *—Si(OR)$_x$(R')$_{3-x}$ residue, in which R and R', independently of one another, denote a (C$_1$ to C$_4$)alkyl group (preferably methyl or ethyl), x denotes 1, 2 or 3;

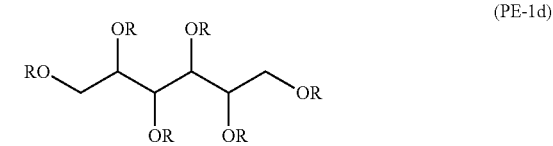

(PE-1d)

in which:

at least three R groups denote a —(CH$_2$CH$_2$O)$_p$—(CHCH$_3$CH$_2$O)$_m$—K-T group and the other R groups denote a hydrogen atom or a —K-T group, in which, independently of one another, p denotes an integer from 1 to 500 and m denotes an integer from 0 to 500, and p and m have a ratio to one another such that there is a maximum proportion of 50 wt. % (preferably a maximum of 40 wt. %, particularly preferably a maximum of 30 wt. %) of propylene oxide units, relative to the weight of the corresponding polyoxyalkylene chain, K denotes a connectivity selected from a covalent bond or from a molecular fragment having two free valences, T denotes a molecular fragment comprising at least one *—Si(OR)$_x$(R')$_{3-x}$ residue, in which R and R', independently of one another, denote a (C$_1$ to C$_4$)alkyl group (preferably methyl or ethyl), x denotes 1, 2 or 3;

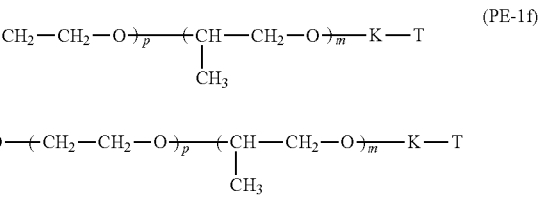

(PE-1f)

in which, independently of one another, p denotes an integer from 1 to 500 and m denotes an integer from 0 to 500, and p and m have a ratio to one another such that there is a maximum proportion of 50 wt. % (preferably a maximum of 40 wt. %, particularly preferably a maximum of 30 wt. %) of propylene oxide units, relative to the weight of the corresponding polyoxyalkylene chain, K independently of one another, denotes a connectivity selected from a covalent bond or from a molecular fragment having two free valences, T independently of one another, denotes a molecular fragment comprising at least one *—Si(OR)$_x$(R')$_{3-x}$ residue, in which R and R', independently of one another, denote a ($C_1$ to $C_4$)alkyl group (preferably methyl or ethyl), x denotes 1, 2 or 3.

The ethylene oxide and propylene oxide units may be randomly distributed, distributed as a gradient or may be present in at least two blocks.

The previously preferred groups K and T apply for formulae (PE-1a) to (PE-1f). The structural fragment —K-T according to formulae (PE-1a) to (PE-1f) most particularly preferably denotes a group

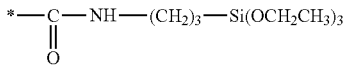

The polyether-modified organic compounds of formula (PE-1) are preferably included in the agents according to the present specification in an amount from 0.01 to 15.0 wt. %, particularly preferably from 0.1 to 8.0 wt. %, most particularly preferably 0.2 to 5.0 wt. %, most preferably from 0.25 to 2.5 wt. %, relative in each case to the total weight of the agent.

Cosmetic agents are preferred according to the present specification which include, in a cosmetically acceptable carrier, (a) polyether-modified organic compounds obtained by reacting
  (i) organic compounds including at least three residues selected from hydroxyl group and/or amino group (preferably selected from hydroxyl group, primary amino group, secondary amino group; particularly preferably hydroxyl group(s)) with
  (ii) at least 3 molar equivalents of at least one polyether of formula (I)

$$\text{T-K-A-K'—Y} \tag{I}$$

in which:

A denotes a polyoxyalkylene chain consisting of ethylene oxide units or ethylene oxide and propylene oxide units, having a maximum proportion of 50 wt. % of propylene oxide units, relative to the weight of A, K and K' independently of one another, denote a connectivity selected from a covalent bond or from a molecular fragment having two free valences, T denotes at least one *—Si(OR)$_x$(R')$_{3-x}$ group, in which R and R', independently of one another, denote a ($C_1$ to $C_4$)alkyl group (in particular methyl or ethyl), x denotes 1, 2 or 3, Y denotes a group that is reactive to hydroxyl groups or amino groups, and (b) at least one polar alkoxysilane compound of formula (SI)

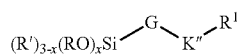 (SI)

in which:

G denotes a ($C_1$ to $C_3$)alkylene group,

K" denotes a connectivity selected from a covalent bond or from a molecular fragment having two free valences, $R^1$ denotes a molecular fragment comprising at least one polar substituent selected from at least one representative of the group formed from
  quaternized ammonium residues
  amino groups
  anionic residues x denotes 1, 2 or 3, R and R' independently of one another, denote a ($C_1$ to $C_4$)alkyl group (in particular methyl or ethyl), and (c) at least one coloring compound.

The specified molar equivalents relate to the amount of substance in the organic compound that was used.

For the residues A, K, K' and T the preferred examples listed under formula (PE-1) apply.

The residue Y according to formula (I) preferably denotes
  an isocyanate group (the isocyanate group is particularly preferred)
  a *—Si(OR)$_x$(R')$_{3-x}$ group in which R and R', independently of one another, denote a ($C_1$ to $C_4$)alkyl group (preferably methyl or ethyl) and x denotes 1, 2 or 3,
  a *—Si(R)$_x$(R')$_{3-x}$ group
    in which R denotes a halogen atom (preferably chlorine or bromine) and R', independently of one another, denotes a ($C_1$ to $C_4$)alkyl group (preferably methyl or ethyl) and x denotes 1, 2 or 3,
  a T-K—C(O)—O—C(O)—* group, in which T and K are as defined according to formula (I),
  a *—C(O)-Hal group, wherein Hal denotes chlorine or bromine,
  an epoxy group,
  a formyl group.

The polyether-modified organic compound of this example is preferably included in the agents according to the present specification in an amount of from 0.01 to 10.0 wt. %, particularly preferably from 0.1 to 2.0 wt. %, most particularly preferably 0.2 to 1.0 wt. %, relative in each case to the total weight of the agent.

The polyethers of formula (I) preferably have a molar mass from 1 to 200 kiloDaltons (kDa), particularly preferably from 1 to 10 kDa.

The polyethers of formula (I) for use in the context of the present specification for producing the polyether-modified compounds of component (a) may be obtained by reacting at least one compound of formula (II):

$$\text{X-A-X'} \tag{II}$$

in which:

A denotes a polyoxyalkylene chain consisting of either ethylene oxide units or both ethylene oxide and propylene oxide units, wherein the polyoxyalkylene chain has a maximum proportion of 50 wt. % of propylene oxide units, relative to the weight of A, X and X' independently of one another, denote a structural fragment including an OH, NH$_2$ or NHR group with at least 2 molar equivalents of a compound of formula (III):

$$\text{Y—K-T} \tag{III}$$

in which:

Y denotes an —OH—, —NH$_2$—, NHR—, NR$_2$-reactive group,

K denotes a connectivity selected from a covalent bond or from a molecular fragment having two free valences, T denotes a molecular fragment comprising at least one —Si(OR)$_x$(R')$_{3-x}$ residue,
  in which R and R', independently of one another, denote a ($C_1$ to $C_4$)alkyl group (preferably methyl or ethyl),
  x denotes 1, 2 or 3.

The specified molar equivalents relate to the amount of substance in the organic compound(s) of formula (II) that are used.

According to the above manufacturing method for producing the compounds of formula (I), dihydroxy-terminated polyoxyalkylene diols, diamino-terminated polyoxyalkylene diamines, monohydroxy-monoamine-terminated polyoxyalkylene-monol monoamines, monohydroxy-monoalkoxy-terminated polyoxyalkylene monols or monoamino-monoalkoxy-terminated polyoxyalkylene monoamines for example are used as compounds of formula (II), the diamines and diols being preferred.

The residues X and X' of formula (II), preferably (and independently of one another) denote OH, $NH_2$ and NHR, particularly preferably OH and $NH_2$.

The residue R in the NHR and $NR_2$ groups of formula (III) preferably denotes a linear or branched alkyl group having from 1 to 10 carbon atoms, preferably from 1 to 6 carbon atoms.

The average molecular weight of the compound of formula (II) is preferably 500 to 30,000 g/mol, particularly preferably 1000 to 20,000, better still 2,000 to 18,000 g/mol, and may be determined by end-group analysis, for example.

For the residues A, K, K' and T the preferred examples listed under formula (PE-1) apply.

Within the context of this example at least one compound of general formula (III-1) is preferably used as the compound of formula (III)

(III-1)

in which:
Y denotes an —OH—, —$NH_2$—, —NHR— and/or —$NR_2$-reactive group (in particular an isocyanate group, a halogen atom, a carboxylic acid anhydride group, a halocarbonyl group (in particular chlorocarbonyl), an epoxy group, a formyl group),
K is defined as for formula (I) (or as for the aforementioned preferred connectivities),
R denotes a ($C_1$ to $C_4$)alkyl group or a ($C_2$ to $C_4$) acyl group (preferably ethyl or methyl),
R' denotes a ($C_1$ to $C_4$)alkyl group (preferably methyl or ethyl),
x denotes 1, 2 or 3.

The compounds of general formula (III-1) include all functional silane derivatives that are capable of reacting with X groups of formula (III-1). Examples are acrylate silanes such as (3-acryloxypropyl)trimethoxysilane, (acryloxymethyl)triethoxysilane and (acryloxymethyl)methyldimethoxysilane, isocyanato silanes such as (3-isocyanatopropyl)trimethoxysilane, (3-isocyanatopropyl)triethoxysilane, (isocyanatomethyl)methyldimethoxysilane and (isocyanatomethyl)trimethoxysilane, aldehyde silanes such as triethoxysilylundecanal and triethoxysilylbutyraldehyde, epoxy silanes such as (3-glycidoxypropyl)trimethoxysilane, anhydride silanes such as 3-(triethoxysilyl)propyl succinic acid anhydride, halosilanes such as chloromethyltrimethoxysilane, 3-chloropropylmethyldimethoxysilane, as well as tetraethyl silicate (TEOS), which is commercially available for example from Wacker Chemie GmbH (Burghausen), Gelest, Inc. (Morrisville, USA) or ABCR GmbH & Co. KG (Karlsruhe) or may be produced by known methods. Isocyanato silanes or anhydride silanes are particularly preferred. If all hydroxyl end groups react completely with isocyanato silanes, completely silylated polyethers are obtained. In such a case the K group includes only the group of atoms located in the starting isocyanato silane between the isocyanato group and the silyl group. If all hydroxyl end groups react completely with anhydride silanes, for example 3-(triethoxysilyl) propyl succinic acid anhydride, completely silylated polyethers are likewise obtained. In such a case the K' group includes only the group of atoms located in the starting anhydride silane between the anhydride group and the silyl group.

If the residues X and X' in general formula (II) denote OH, $NH_2$ or NHR, the reaction with the compounds of general formula (III) or (III-1) may take place either with cleavage of the HY compound—as for example in the case of the reaction of an OH group with a monohalosilane (K=direct bond)—or with addition—as for example in the case of the reaction of an OH group with an isocyanatoalkyl silane (formation of a urethane).

The residues X and X' of formula (II), preferably (and independently of one another) denote OH, $NH_2$ and NHR, particularly preferably OH and $NH_2$.

The residue R in the NHR, $NR_2$ and OR groups of formula (III-1) preferably denotes a linear or branched alkyl group having from 1 to 10 carbon atoms, preferably from 1 to 6 carbon atoms.

In the reaction between the compounds of formula (I) and the compounds of formula (II), at least one hydrogen atom, preferably up to four hydrogen atoms of the OH and/or $NH_2$ groups, are each reacted with a molecule of the compound of general formula (II), such that at least monosilylated, in the case of the diamino compounds of general formula (I) up to tetrasilylated, polyethers are formed.

Most particularly preferred polyethers for producing the polyether-modified organic compounds according to the present specification are selected from at least one compound of formula (I-1a) or (I-1b)

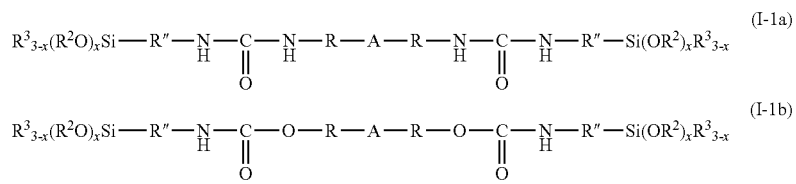

in which:
A denotes a polyoxyalkylene chain consisting of ethylene oxide units or ethylene oxide and propylene oxide units, having a maximum proportion of 50 wt. % of propylene oxide units, relative to the weight of A,
R and R'' independently of one another, denote methylene, ethane-1-diyl, propane-1,2-diyl, propane-1,3-diyl, butane-1,2-diyl, butane-1,3-diyl, butane-1,4-diyl, phenylene,
$R^1$ denotes a ($C_1$ to $C_6$)alkyl group, a hydrogen atom or an $R^3_{3-x}(R^2O)_xSi$—K— group,
$R^2$ denotes a ($C_1$ to $C_4$)alkyl group (preferably methyl or ethyl),
$R^3$ denotes a ($C_1$ to $C_6$)alkyl group or an aryl group (preferably methyl),
x denotes 1, 2 or 3 (in particular 3).

Within the context of a preferred example, said water-soluble, polyether-modified organic polymer having at least one polyether structural unit is selected from one or more linear polyethers of formula (PE-2)

T-K-A-K'-T' (PE-2)

in which:
A denotes a polyoxyalkylene chain consisting of either ethylene oxide units or both ethylene oxide and propylene oxide units, wherein the polyoxyalkylene chain has a maximum proportion of 50 wt. % of propylene oxide units, relative to the weight of A,
K and K' independently of one another, denote a connectivity selected from a covalent bond or from a molecular fragment having two free valences,
T and T' denote a molecular fragment comprising at least one —Si(OR)$_x$(R')$_{3-x}$ residue,
in which R and R', independently of one another, denote a (C$_1$ to C$_4$)alkyl group (preferably methyl or ethyl),
x denotes 1, 2 or 3.

Most particularly preferred linear polyethers are selected from at least one compound of formulae (PE-2a), (PE-2b), (PE-2c), (PE-2d) or (PE-2e):

$$R^1-A-K-Si(OR^2)_xR^3_{3-x} \tag{PE-2a}$$

$$R^1-A-R-O-\underset{\underset{O}{\|}}{C}-\underset{H}{N}-R''-Si(OR^2)_xR^3_{3-x} \tag{PE-2b}$$

$$R^1-A-R-\underset{H}{N}-\underset{\underset{O}{\|}}{C}-\underset{H}{N}-R''-Si(OR^2)_xR^3_{3-x} \tag{PE-2c}$$

$$R^3_{3-x}(R^2O)_xSi-R''-\underset{H}{N}-\underset{\underset{O}{\|}}{C}-\underset{H}{N}-R-A-R-\underset{H}{N}-\underset{\underset{O}{\|}}{C}-\underset{H}{N}-R''-Si(OR^2)_xR^3_{3-x} \tag{PE-2d}$$

$$R^3_{3-x}(R^2O)_xSi-R''-\underset{H}{N}-\underset{\underset{O}{\|}}{C}-O-R-A-R-O-\underset{\underset{O}{\|}}{C}-\underset{H}{N}-R''-Si(OR^2)_xR^3_{3-x} \tag{PE-2e}$$

in which:
A denotes a polyoxyalkylene chain consisting of either ethylene oxide units or both ethylene oxide and propylene oxide units, wherein the polyoxyalkylene chain has a maximum proportion of 50 wt. % of propylene oxide units, relative to the weight of A,
K denotes a covalent bond, an oxy group, an imino group or at least one of the following connectivities (K1) to (K10)

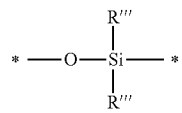  (K1)

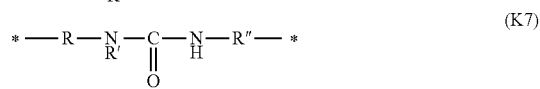  (K2)

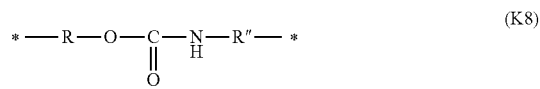  (K3)

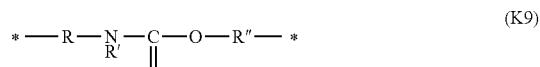  (K4)

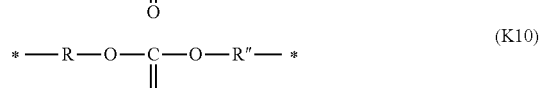  (K5)

$$*-O-\underset{\underset{R'''}{|}}{\overset{\underset{R'''}{|}}{Si}}-* \tag{K6}$$

$$*-R-\underset{R'}{N}-\underset{\underset{O}{\|}}{C}-\underset{H}{N}-R''-* \tag{K7}$$

$$*-R-O-\underset{\underset{O}{\|}}{C}-\underset{H}{N}-R''-* \tag{K8}$$

$$*-R-\underset{R'}{N}-\underset{\underset{O}{\|}}{C}-O-R''-* \tag{K9}$$

$$*-R-O-\underset{\underset{O}{\|}}{C}-O-R''-* \tag{K10}$$

in which:
R and R" independently of one another, denote methylene, ethane-1,2-diyl, propane-1,2-diyl, propane-1,3-diyl, butane-1,2-diyl, butane-1,3-diyl, butane-1,4-diyl, phenylene and
R' denotes a hydrogen atom or a (C$_1$ to C$_4$)alkyl group,
R'" independently of one another, denotes a (C$_1$ to C$_4$)alkyl group or an aryl group.
R and R" independently of one another, denote methylene, ethane-1,2-diyl, propane-1,2-diyl, propane-1,3-diyl, butane-1,2-diyl, butane-1,3-diyl, butane-1,4-diyl, phenylene,
R$^1$ denotes an R$^3_{3-x}$(R$^2$O)$_x$Si—K— group,
R$^2$ denotes a (C$_1$ to C$_4$)alkyl group (preferably methyl or ethyl),
R$^3$ denotes a (C$_1$ to C$_6$)alkyl group or an aryl group (preferably methyl),
x denotes 1, 2 or 3 (preferably 3).

According to formula (PE-2) or formula (PE-2a) to (PE-2e), A thus preferably denotes a structural fragment of formula (A1):

$$*-(OCH_2CH_2)_n-(OCH_2CH(CH_3))_m-* \tag{A1}$$

in which:
n denotes an integer from 100 to 10,000,
m denotes an integer from 0 to 10,000, and
the structural fragment of formula (A1) has a maximum proportion of 50 wt. % of propylene oxide units, relative to the weight of the structural fragment (A1).

The polyether-modified organic compounds of formula (PE-2) are preferably included in the agents according to the present specification in an amount from 0.01 to 15.0 wt. %, particularly preferably from 0.1 to 8.0 wt. %, most particularly preferably 0.2 to 5.0 wt. %, most preferably from 0.25 to 2.5 wt. %, relative in each case to the total weight of the agent.

Within the context of a further example, said water-soluble polymer of component (a) is selected from solid particles which (i) are surface-modified with polyethers, wherein the polyethers include a polyoxyalkylene chain consisting of either ethylene oxide units or both ethylene oxide and propylene oxide units, wherein the polyoxyalkylene chain has a maximum proportion of 50 wt. % of propylene oxide units, relative to the weight of the polyoxyalkylene chain, (ii) have at least one *—Si(OR)$_x$(R')$_{3-x}$ residue, in which R and R', independently of one another, denote a (C$_1$ to C$_4$)alkyl group (preferably methyl or ethyl), x denotes 1, 2 or 3.

The skeleton of the solid particles is preferably selected from aluminates, silicates, aluminum silicates, zinc oxide, titanium dioxide and SiO$_2$, in particular from aluminates, silicates, aluminum silicates and silica gel. Mixtures of these preferred or particularly preferred solid particles are likewise in accordance with the present specification.

Particularly preferred aluminates are selected from alpha-aluminum oxide, beta-aluminum oxide, gamma-aluminum oxide and mixtures thereof.

Particularly preferred aluminum silicates (also known as alumosilicates) are selected from phyllosilicates, and tectosilicates.

Preferably suitable phyllosilicates are selected from kaolins (in particular from kaolinite, dickite, hallosite and nacrite), serpentine, talc, pyrophyllite, montmorillonite, quartz, bentonite, and mica (in particular from illite, muscovite, paragonite, phlogopite, biotite, lepidolite, margarite, smectite (in particular from montmorillonite, saponite, nontronite, and hectorite)).

Preferably suitable tectosilicates are selected from feldspar minerals (in particular albite, orthoclase, anorthite, leucite, sodalite, hauyne, labradorite, lazurite, nosean, nepheline), and zeolites.

Zeolites are natural or synthetic crystalline aluminum silicates of alkali or alkaline-earth metals. Zeolites consist of SiO$_4$ and AlO$_4$ tetrahedra, which are connected by four-, six-, eight- or twelve-membered oxygen rings, giving rise to cavities which extend throughout the entire zeolite crystal. The preferred zeolites include zeolites of type A, K, L, P-L, O, T, X, Y and Ω as well as mixtures thereof. Particularly preferred zeolites are selected in particular from zeolite A (in particular from Na$_{12}$[(AlO$_2$)$_{12}$(SiO$_2$)$_{12}$]), Ca$_5$Na$_5$[(AlO$_2$)$_{12}$(SiO$_2$)$_{12}$], [K$_{12}$[(AlO$_2$)$_{12}$(SiO$_2$)$_{12}$]), zeolite X (in particular from Na$_{86}$[(AlO$_2$)$_{86}$(SiO$_2$)$_{106}$]), Ca$_{40}$Na$_6$[(AlO$_2$)$_{86}$(SiO$_2$)$_{106}$)], Sr$_{21}$Ba$_{22}$[(AlO$_2$)$_{86}$(SiO$_2$)$_{106}$]), zeolite Y (in particular from Na$_{56}$[(AlO$_2$)$_{56}$(SiO$_2$)$_{136}$], Na$_{56}$[(AlO$_2$)$_{56}$(SiO$_2$)$_{136}$]), ZSM-5 (in particular from Na$_3$[(AlO$_2$)$_3$(SiO$_2$)$_{93}$]), mordenite, and silicalite (SiO$_2$)$_{96}$.

Cosmetic agents are preferred according to the present specification which include, in a cosmetically acceptable carrier, (a) polyether-modified solid particles obtained by reacting hydroxyl group-containing solid particles with at least one polyether of formula (I)

$$T-K-A-K'-T' \qquad (I)$$

in which:

A denotes a polyoxyalkylene chain consisting of either ethylene oxide units or both ethylene oxide and propylene oxide units, wherein the polyoxyalkylene chain has a maximum proportion of 50 wt. % of propylene oxide units, relative to the weight of A, K and K' independently of one another, denote a connectivity selected from a covalent bond or from a molecular fragment having two free valences, T and T' independently of one another, denote a molecular fragment comprising at least one —Si(OR)$_x$(R')$_{3-x}$ residue, in which R and R', independently of one another, denote a (C$_1$ to C$_4$)alkyl group (preferably methyl or ethyl), x denotes 1, 2 or 3, wherein at most one residue out of T or T' may additionally denote a (C$_1$-C$_6$)alkyl group, an aryl group, an aryl(C$_1$ to C$_6$)alkyl group, a (C$_1$ to C$_6$)alkoxy group or a (C$_2$ to C$_6$) acyl group, and (b) at least one polar alkoxysilane compound of formula (SI)

(SI)

in which:

G denotes a (C$_1$ to C$_3$)alkylene group,

K'' denotes a connectivity selected from a covalent bond or from a molecular fragment having two free valences, R$^1$ denotes a molecular fragment comprising at least one polar substituent selected from at least one representative of the group consisting of quaternized nitrogen atoms, amino groups, and anionic residues.

x denotes 1, 2 or 3,

R and R' independently of one another, denote a (C$_1$ to C$_4$)alkyl group (preferably methyl or ethyl), and (c) at least one coloring compound.

The polyether-modified solid particles are preferably included in the agents according to the present specification in an amount from 0.01 to 15.0 wt. %, preferably from 0.1 to 8.0 wt. %, particularly preferably 0.2 to 5.0 wt. %, most preferably from 0.25 to 2.5 wt. %, relative in each case to the total weight of the agent.

The cosmetic agent according to the present specification includes a component (b), which may be at least one polar alkoxysilane compound of formula (SI)

(SI)

in which the residues G, K'', R$^1$, R, R' and the number x are as previously defined (see above).

To compensate for the cationic charge of the residue R$^1$, the agent according to the present specification includes an equivalent of corresponding anions. Inorganic and organic anions are suitable, such as for example chloride, bromide, methyl sulfate, sulfate, hydrogen sulfate, methyl sulfate, triflate, toluenesulfonate, tetrafluoroborate.

It is preferable according to the present specification if, according to formula (SI), the residue R' denotes a methyl group and the residue R denotes an ethyl group.

The residue K" according to formula (SI) preferably denotes a covalent bond, an oxy group, a ($C_1$ to $C_6$)alkylene group, an imino group or at least one of the following connectivities (K1) to (K10)

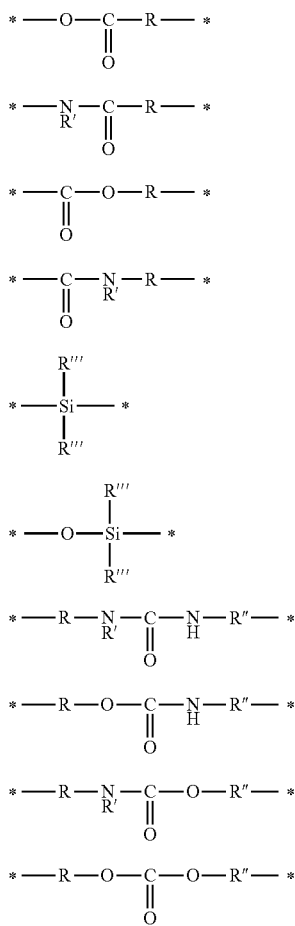

in which:
R and R" independently of one another, denote methylene, ethane-1,2-diyl, propane-1,2-diyl, propane-1,3-diyl, butane-1,2-diyl, butane-1,3-diyl, butane-1,4-diyl or phenylene,
R' denotes a hydrogen atom or a ($C_1$ to $C_4$)alkyl group,
R''' independently of one another, denotes a ($C_1$ to $C_4$)alkyl group or an aryl group.

The residue G according to formula (SI) preferably denotes a methylene group or a propane-1,3-diyl group, particularly preferably a propane-1,3-diyl group.

The residue $R^1$ of formula (SI) particularly preferably comprises at least one quaternized nitrogen atom.

To produce the compounds according to formula (SI), at least one compound of formula (III)

$$Y-K-Si(OR)_x(R')_{3-x} \quad (III)$$

in which:
Y denotes an —OH—, —$NH_2$—, NHR—, $NR_2$-reactive group,
K denotes a connectivity selected from a covalent bond or from a molecular fragment having two free valences,
R and R' independently of one another, denote a ($C_1$ to $C_4$)alkyl group (preferably methyl or ethyl),
x denotes 1, 2 or 3,
is reacted with at least one compound of formula (IV), $$Z-R^2 \quad (IV)$$

in which:
Z denotes an —OH, —$NH_2$, NHR, $NR_2$ group,
$R^2$ denotes a molecular fragment comprising at least one polar substituent selected from at least one representative of the group consisting of
  quaternized nitrogen atoms (preferably residue $R^2$ according to formula (SI-1) (see below)),
  amino groups, and
  anionic residues.

Preferred compounds of formula (III) which may be used are the aforementioned compounds of formula (III-1) and the representatives thereof described as being particularly preferred (see above).

If the residue Z in general formula (IV) denotes OH, $NH_2$ or NHR, the reaction with the compounds of general formula (III) or (III-1) may take place either with cleavage of the HY compound—as for example in the case of the reaction of an OH group with a monohalosilane (K=direct bond)—or with addition—as for example in the case of the reaction of an OH group with an isocyanatoalkyl silane (formation of a urethane).

The residue Z of formula (IV) preferably denotes OH, $NH_2$ and NHR, particularly preferably OH or $NH_2$.

Within the context of a particularly preferred example of the alkoxysilanes according to the present specification of formula (SI), at least one molecular fragment $R^1$ of formula (SI) (and likewise $R^2$ of formula (IV) for the aforementioned manufacturing method) includes at least one quaternized nitrogen atom.

It is also particularly preferable for the molecular fragment $R^1$ of formula (SI) (and likewise $R^2$ of formula (IV) for the aforementioned manufacturing method) to include in addition to at least one quaternized nitrogen atom additionally at least one hydrocarbon residue bound thereto having 8 to 20 carbon atoms.

Most particularly preferred agents according to the present specification include as the polar alkoxysilane of formula (SI) at least one compound of formula (SI-1)

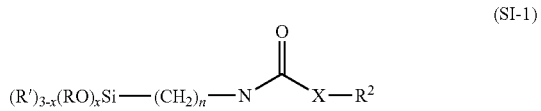

in which:
R and R' independently of one another, denote a ($C_1$ to $C_4$)alkyl group (preferably methyl or ethyl),
x denotes 1, 2 or 3,
n denotes 1, 2 or 3,
X denotes an oxygen atom or an NH group,
$R^2$ denotes a *—$(CH_2)_m$—$N^+R^3R^4R^5$ group in which
  m denotes 2, 3, 4, 5 or 6,
  $R^3$, $R^4$ and $R^5$, independently of one another, denote ($C_1$ to $C_{20}$)alkyl, ($C_8$ to $C_{20}$) acyloxy($C_2$ to $C_3$)alkyl, ($C_2$ to $C_{20}$)alkenyl, ($C_8$ to $C_{20}$)alkanamido($C_2$ to $C_3$)alkyl or aryl($C_1$ to $C_4$)alkyl.

It is in turn particularly preferable for the molecular fragment $R^2$ of formula (SI-1) to include in addition to at least one quaternized nitrogen atom additionally at least one hydrocarbon residue bound thereto having 8 to 20 carbon atoms.

According to formula (SI-1) and formula (IV) above $R^2$ preferably denotes an (N,N,N-tri($C_1$ to $C_{20}$)alkyl azaniumyl) ($C_2$ to $C_6$)alkyl group, an (N-[($C_8$ to $C_{20}$) acyloxy($C_2$ to $C_3$)alkyl]-N,N-dimethyl azaniumyl) ($C_2$ to $C_6$)alkyl group, an (N,N-di[($C_8$ to $C_{20}$)acyloxy($C_2$ to $C_3$)alkyl]-N-methyl] azaniumyl) ($C_2$ to $C_6$)alkyl group, an (N,N-dimethyl-N—($C_2$ to $C_{20}$)alkyl azaniumyl) ($C_2$ to $C_6$)alkyl group, (N,N-dimethyl-N-benzyl azaniumyl) ($C_2$ to $C_6$)alkyl group, (N,N-dimethyl-N—($C_8$ to $C_{20}$)alkanamido($C_2$ to $C_3$)alkyl azaniumyl) ($C_2$ to $C_6$)alkyl group or (N-methyl-N,N-di($C_8$ to $C_{20}$)alkanamidoethyl azaniumyl) ($C_2$ to $C_3$)alkyl group.

To compensate for the cationic charge of the residue $R^2$ the agent according to the present specification includes corresponding anions.

Within the context of a preferred example of the alkoxysilanes according to the present specification of formula (SI) at least one molecular fragment $R^1$ of formula (SI) (and likewise $R^2$ of formula (IV) for the aforementioned manufacturing method) includes at least one amino group, preferably at least one tertiary amino group.

It is in turn particularly preferable for the molecular fragment $R^1$ of formula (SI) (and likewise $R^2$ of formula (IV) for the aforementioned manufacturing method) to include in addition to at least one quaternized nitrogen atom additionally at least one hydrocarbon residue bound thereto having 8 to 20 carbon atoms.

Preferred agents according to the present specification include as the polar alkoxysilane of formula (SI) at least one compound of formula (SI-1a)

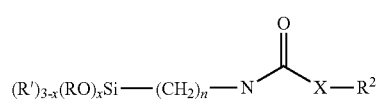
(SI-1a)

in which:
R and R' independently of one another, denote a ($C_1$ to $C_4$)alkyl group (preferably methyl or ethyl),
x denotes 1, 2 or 3,
n denotes 1, 2 or 3,
X denotes an oxygen atom or an NH group,
$R^2$ denotes a *—$(CH_2)_m$—$NR^3R^4$ group, in which
    m denotes 2, 3, 4, 5 or 6,
    $R^3$ and $R^4$, independently of one another, denote ($C_1$ to $C_{20}$)alkyl, ($C_8$ to $C_{20}$) acyloxy($C_2$ to $C_3$)alkyl, ($C_2$ to $C_{20}$)alkenyl, ($C_8$ to $C_{20}$)alkanamido($C_2$ to $C_3$)alkyl or aryl($C_1$ to $C_4$)alkyl.

It is in turn preferable for the molecular fragment $R^2$ of formula (SI-1a) to include in addition to at least one said amino group additionally at least one hydrocarbon residue bound thereto having 8 to 20 carbon atoms.

According to formula (SI-1a) and formula (IV) above $R^2$ preferably denotes an (N,N-di($C_1$ to $C_{20}$)alkylamino) ($C_2$ to $C_6$)alkyl group, an (N—[($C_8$ to $C_{20}$) acyloxy($C_2$ to $C_3$)alkyl]-N-methylamino) ($C_2$ to $C_6$)alkyl group, an (N,N-di[($C_8$ to $C_{20}$)acyloxy($C_2$ to $C_3$)alkyl]amino($C_2$ to $C_6$)alkyl group, an (N-methyl-N—($C_8$ to $C_{20}$)alkylamino) ($C_2$ to $C_6$)alkyl group, (N-methyl-N-benzylamino) ($C_2$ to $C_6$)alkyl group, (N-methyl-N—($C_8$ to $C_{20}$)alkanamido($C_2$ to $C_3$)alkylamino) ($C_2$ to $C_6$)alkyl group or (N,N-di($C_8$ to $C_{20}$)alkanamidoethyl amino) ($C_2$ to $C_3$)alkyl group.

Said polar trialkoxysilane compounds are preferably selected from the following compounds of formula (SI-1b)

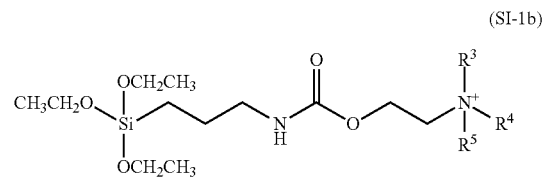
(SI-1b)

in which:
$R^3$ denotes methyl, ethyl or benzyl,
$R^4$ and $R^5$ independently of one another, denote a methyl group, an ethyl group, a ($C_8$ to $C_{22}$)alkyl group, a ($C_8$ to $C_{22}$)alkenyl group, a 2-(($C_8$ to $C_{22}$)alkyl carbonyloxy)ethyl group, a 2-(($C_8$ to $C_{22}$)alkenyl carbonyloxy)ethyl group, a ($C_8$ to $C_{22}$)alkylamido($C_2$ to $C_3$)alkyl group.

Of those, the trialkoxysilane compound is in turn preferably selected from formulae (SI-1c) to (SI-1f):

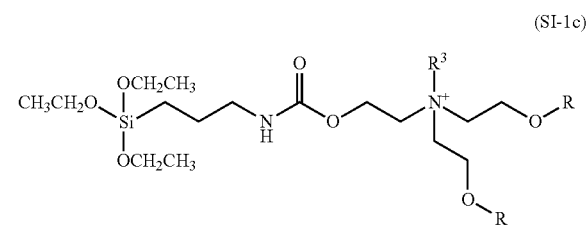
(SI-1c)

in which R denotes a ($C_8$ to $C_{22}$) acyl group and $R^3$ denotes methyl, ethyl or benzyl (preferably methyl);

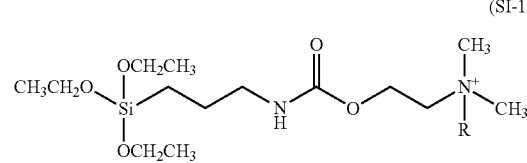
(SI-1d)

in which R denotes a ($C_8$ to $C_{22}$)alkyl group;

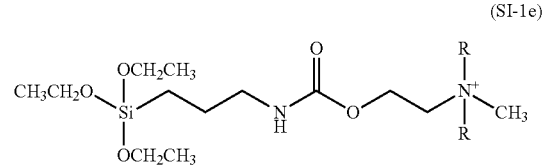
(SI-1e)

in which R in each case denotes a ($C_8$ to $C_{22}$)alkyl group;

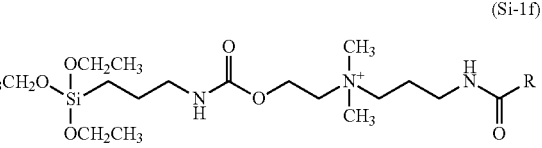
(Si-1f)

in which R denotes a ($C_8$ to $C_{22}$)alkyl group.

Within the context of an example of the alkoxysilanes according to the present specification, at least one molecular fragment $R^1$ of formula (SI) (and likewise $R^2$ of formula (IV) for the manufacturing method described) includes at least one anionic group.

According to the present specification the molecular fragments $R^1$ of formula (SI) and $R^2$ of formula (IV) and $R^2$ of formula (SI-1), each having at least one anionic group, are preferably a molecular fragment including 1 to 5, preferably 3, 4 or 5, deprotonatable acid groups. The anionic groups or the deprotonatable acid groups of said molecular fragments $R^1$ of formula (SI) and $R^2$ of formula (IV) and $R^2$ of formula (Si-1) are preferably selected from carboxyl group and/or sulfonic acid group and/or phosphate or the salt forms thereof (in particular carboxyl group and/or sulfonic acid group or the salt forms thereof, particularly preferably carboxyl group or the salt form thereof).

In a possible example the molecular fragment $R^1$ of formula (SI) and $R^2$ of formula (IV) and $R^2$ of formula (SI-1) includes at least one, preferably at least two, particularly preferably 1 to 5, above all 2 to 5, in particular 2, 3, 4 or 5 carboxymethyl units. In a most particularly preferred example said molecular fragment is an ethylenediamine triacetate unit that is covalently bound to the connectivity K" of formula (SI) via one of its nitrogen atoms.

The molecular fragment $R^1$ of formula (SI) preferably includes a group $$*-B-[(N(CH_2COOM)-B')_y-N(CH_2COOM)_2]$$

in which:
B denotes a ($C_1$ to $C_6$)alkylene residue (preferably ethane-1,2-diyl, propane-1,2-diyl, propane-1,3-diyl, butane-1,2-diyl, butane-1,3-diyl, butane-1,4-diyl),
B' denotes a ($C_1$ to $C_6$)alkylene residue (preferably ethane-1,2-diyl, propane-1,2-diyl, propane-1,3-diyl, butane-1,2-diyl, butane-1,3-diyl, butane-1,4-diyl),
M independently of one another, denotes a hydrogen atom or an equivalent of a monovalent or polyvalent cation,
y denotes 1 or 2 (preferably 1).

If the above group is present in acid form, the residue M denotes a hydrogen atom. In that case the —COOH fragments form a carboxyl group. If the above group is present in salt form (carboxylate), M denotes an equivalent of a monovalent or polyvalent cation. For reasons of electroneutrality the mono- or polyvalent cation $M^{z+}$ having a charge number z of one or more serves only to compensate for the simple negative charge of the carboxylate that is present during salt formation. The equivalent of the corresponding cation which is to be used for this purpose is 1/z. In the case of salt formation the fragment —COOM denotes the group:

$$—COO^-1/z(M^{z+})$$

In principle, all physiologically acceptable cations are suitable as mono- or polyvalent cations $M^{z+}$. In particular these are metal cations of the physiologically acceptable metals from groups Ia, Ib, IIa, IIb, IIIb, VIa or VIII of the periodic table, ammonium ions, as well as cationic organic compounds having a quaternized nitrogen atom. The quaternized nitrogen atom is formed, for example, by protonation of primary, secondary or tertiary organic amines with an acid, such as for example with compounds of the above group $R^d$ in its acid form, or by permanent quaternization of said organic amines. Examples of these cationic organic ammonium compounds are 2-ammonioethanol and 2-trimethyl ammonioethanol. M preferably denotes a hydrogen atom, an ammonium ion, an alkali metal ion, a half equivalent of an alkaline-earth metal ion or a half equivalent of a zinc ion, particularly preferably a hydrogen atom, an ammonium ion, a sodium ion, a potassium ion, ½ calcium ion, ½ magnesium ion or ½ zinc ion.

A preferred molecular fragment $R^1$ of formula (SI) obeys the general formula $$*-B-[(N(CH_2COOM)-B')_y-N(CH_2COOM)_2]$$

in which:
B denotes a ($C_1$ to $C_6$)alkylene residue (preferably ethane-1,2-diyl, propane-1,2-diyl, propane-1,3-diyl, butane-1,2-diyl, butane-1,3-diyl, butane-1,4-diyl),
B' denotes a ($C_1$ to $C_6$)alkylene residue (preferably ethane-1,2-diyl, propane-1,2-diyl, propane-1,3-diyl, butane-1,2-diyl, butane-1,3-diyl, butane-1,4-diyl) or an N,N-bis($C_1$ to $C_6$)alkylene-N-carboxymethyl,
M independently of one another, denotes a hydrogen atom or an equivalent of a monovalent or polyvalent cation,
y denotes 1 or 2 (preferably 1).

All that has been stated in respect of residue M of the above formula also applies here (see above).

Particularly preferred agents of this example have polyether-modified organic compounds including at least one polyether having at least one molecular fragment $R^1$ in formula (SI) of said general formula $$*-B-[(N(CH_2COOM)-B')_y-N(CH_2COOM)_2]$$

Particularly preferred molecular fragments R' of formula (SI) of formula $*-B-[(N(CH_2COOM)-B')_y-N(CH_2COOM)_2]$ are selected from at least one representative of the group formed from 3-N-carboxylmethyl-N-(2'-N',N'-di(carboxymethylamino)ethyl)aminopropyl (B=propane-1,3-diyl, B'=ethane-1,2-diyl, y=1, M as above), 3-N-carboxylmethyl-N-(2'-N',N'-di(carboxymethylamino)ethyl)-N"-carboxymethylaminoethyl)aminopropyl (B=propane-1,3-diyl, B'=ethane-1,2-diyl, y=2, M as above). 3-N-Carboxylmethyl-N-(2'-N',N'-di(carboxymethylamino)ethyl)aminopropyl is most particularly preferred.

Most particularly preferred polar alkoxysilanes are selected from at least one compound of formula (SI-2)

(SI-2)

$$R^3_{3-x}(R^2O)_xSi-K-O-\underset{R}{\underset{|}{\overset{R}{\overset{|}{Si}}}}-B-N\underset{B'}{\diagdown}\diagup^{COOM}_{N\diagup^{COOM}_{\diagdown COOM}}$$

in which:
B denotes a ($C_1$ to $C_6$)alkylene residue (preferably ethane-1,2-diyl, propane-1,2-diyl, propane-1,3-diyl, butane-1,2-diyl, butane-1,3-diyl, butane-1,4-diyl),
B' denotes a ($C_1$ to $C_6$)alkylene residue (preferably ethane-1,2-diyl, propane-1,2-diyl, propane-1,3-diyl, butane-1,2-diyl, butane-1,3-diyl, butane-1,4-diyl) or an N,N-bis($C_1$ to $C_6$)alkylene-N-carboxymethyl,
M independently of one another, denotes a hydrogen atom or an equivalent of a monovalent or polyvalent cation,
$R^2$ and $R^3$ independently of one another, denote a ($C_1$ to $C_4$)alkyl group (preferably methyl or ethyl),
x denotes an integer 1, 2 or 3 (in particular 3),
K denotes a connectivity selected from a covalent bond or from a molecular fragment having two free valences, R independently of one another, denotes a ($C_1$ to $C_4$)alkyl group (in particular methyl or ethyl) or a ($C_1$ to $C_6$)alkoxy group (preferably methoxy or ethoxy).

The preferred examples with respect to the aforementioned preferred features for B, B', M and R apply with the necessary changes in formula (SI-2) above.

The coloring compounds within the meaning of the present specification are preferably selected from:
(1) at least one oxidation dye precursor of the developer component type and optionally additionally at least one coupler component
and/or
(2) at least one substantive dye
and/or
(3) at least one precursor of nature-analogous dyes.

It is preferable according to the present specification to use a p-phenylenediamine derivative or one of its physiologically acceptable salts as the developer component. p-Phenylenediamine derivatives of formula (E1) are particularly preferred

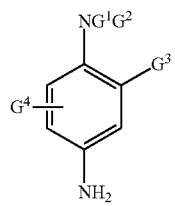

(E1)

in which:
G$^1$ denotes a hydrogen atom, a ($C_1$ to $C_4$)alkyl residue, a ($C_1$ to $C_4$)monohydroxyalkyl residue, a ($C_2$ to $C_4$)polyhydroxyalkyl residue, a ($C_1$ to $C_4$)alkoxy($C_1$ to $C_4$)alkyl residue, a 4'-aminophenyl residue or a ($C_1$ to $C_4$)alkyl residue, which is substituted with a nitrogen-containing group, a phenyl residue or a 4'-aminophenyl residue;
G$^2$ denotes a hydrogen atom, a ($C_1$ to $C_4$)alkyl residue, a ($C_1$ to $C_4$)monohydroxyalkyl residue, a ($C_2$ to $C_4$)polyhydroxyalkyl residue, a ($C_1$ to $C_4$)alkoxy($C_1$ to $C_4$)alkyl residue or a ($C_1$ to $C_4$)alkyl residue, which is substituted with a nitrogen-containing group;
G$^3$ denotes a hydrogen atom, a halogen atom, such as a chlorine, bromine, iodine or fluorine atom, a ($C_1$ to $C_4$)alkyl residue, a ($C_1$ to $C_4$)monohydroxyalkyl residue, a ($C_2$ to $C_4$)polyhydroxyalkyl residue, a ($C_1$ to $C_4$) hydroxyalkyl residue, a ($C_1$ to $C_4$)alkoxy($C_1$ to $C_4$)alkyl residue, a ($C_1$ to $C_4$) acetyl aminoalkoxy residue, a mesylamino($C_1$ to $C_4$)alkoxy residue or a ($C_1$ to $C_4$) carbamoyl aminoalkoxy residue;
G$^4$ denotes a hydrogen atom, a halogen atom, a ($C_1$ to $C_4$)alkyl residue or a ($C_1$ to $C_4$)alkoxy($C_1$ to $C_4$)alkyl residue, or
if G$^3$ and G$^4$ are in ortho-position to one another, they may together form a bridging α,ω-alkylene dioxo group, such as for example an ethylene dioxy group.

Particularly preferred p-phenylenediamines of formula (E1)) are selected from one or more compounds of the group formed from p-phenylenediamine, p-toluylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis-(β-hydroxyethyl)-p-phenylenediamine, 4-N,N-bis-(β-hydroxyethyl)amino-2-methylaniline, 4-N,N-bis-(β-hydroxyethyl)amino-2-chloroaniline, 2-(β-hydroxyethyl)-p-phenylenediamine, 2-(α,β-dihydroxyethyl)-p-phenylenediamine, 2-fluoro-p-phenylenediamine, 2-isopropyl-p-phenylenediamine, N-(β-hydroxypropyl)-p-phenylenediamine, 2-hydroxymethyl-p-phenylenediamine, N,N-dimethyl-3-methyl-p-phenylenediamine, N,N-(ethyl, β-hydroxyethyl)-p-phenylenediamine, N-(β,γ-dihydroxypropyl)-p-phenylenediamine, N-(4'-aminophenyl)-p-phenylenediamine, N-phenyl-p-phenylenediamine, 2-(β-hydroxyethyloxy)-p-phenylenediamine, 2-methoxymethyl-p-phenylenediamine, 2-(β-acetylaminoethyloxy)-p-phenylenediamine, N-(β-methoxyethyl)-p-phenylenediamine, N-(4-amino-3-methylphenyl)-N-[3-(1H-imidazol-1-yl)propyl]amine, 5,8-diaminobenzo-1,4-dioxane as well as the physiologically acceptable salts thereof.

Most particularly preferred p-phenylenediamine derivatives of formula (E1)) according to the present specification are selected from at least one compound of the group p-phenylenediamine, p-toluylenediamine, 2-(β-hydroxyethyl)-p-phenylenediamine, 2-(α,β-dihydroxyethyl)-p-phenylenediamine, N,N-bis-(β-hydroxyethyl)-p-phenylenediamine, 2-methoxymethyl-p-phenylenediamine, N-(4-amino-3-methylphenyl)-N-[3-(1H-imidazol-1-yl)propyl]amine, as well as the physiologically acceptable salts of these compounds.

It may be preferable according to the present specification to use as the developer component compounds including at least two aromatic nuclei which are substituted with amino and/or hydroxyl groups.

Of the binuclear developer components which may be used in the coloring compositions according to the present specification, the compounds corresponding to the following formula (E2) and the physiologically acceptable salts thereof may be cited in particular:

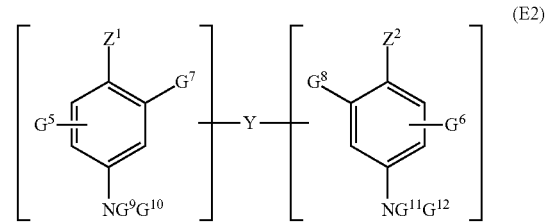

(E2)

in which:
Z$^1$ and Z$^2$, independently of one another, denote a hydroxyl or NH$_2$ residue, which is optionally substituted by a ($C_1$ to $C_4$)alkyl residue, by a ($C_1$ to $C_4$) hydroxyalkyl residue and/or by a bridge Y or which is optionally part of a bridging ring system,
the bridge Y denotes an alkylene group having 1 to 14 carbon atoms, such as for example a linear or branched alkylene chain or alkylene ring, which may be interrupted or terminated by one or more nitrogen-containing groups and/or by one or more heteroatoms such as oxygen, sulfur or nitrogen atoms and may optionally be substituted by one or more hydroxyl or ($C_1$ to $C_8$)alkoxy residues, or a direct bond,
G$^5$ and G$^6$, independently of one another, denote a hydrogen or halogen atom, a ($C_1$ to $C_4$)alkyl residue, a ($C_1$ to $C_4$)monohydroxyalkyl residue, a ($C_2$ to $C_4$)polyhydroxyalkyl residue, a ($C_1$ to $C_4$)aminoalkyl residue or a direct bond to the bridge Y, $G^7$, $G^8$, $G^9$, $G^{10}$, $G^{11}$ and $G^{12}$, independently of one another, denote a hydrogen atom, a direct bond to the bridge Y or a ($C_1$ to $C_4$)alkyl residue, with the proviso that the compounds of formula (E2) include only one bridge Y per molecule.

The substituents used in formula (E2) are defined according to the present specification in an analogous manner to the above statements.

Preferred binuclear developer components of formula (E2) are selected in particular from at least one of the following compounds: N,N'-bis-(β-hydroxyethyl)-N,N'-bis-(4'-aminophenyl)-1,3-diaminopropan-2-ol, N,N'-bis-(β-hydroxyethyl)-N,N'-bis-(4'-aminophenyl)ethylenediamine, N,N'-bis-(4'-aminophenyl)tetramethylenediamine, N,N'-bis-(β-hydroxyethyl)-N,N'-bis-(4'-aminophenyl) tetramethylenediamine, N,N'-bis-(4-(methylamino)phenyl) tetramethylenediamine, N,N'-diethyl-N,N'-bis-(4'-amino-3'-methylphenyl)ethylenediamine, bis-(2-hydroxy-5-aminophenyl)methane, N,N'-bis-(4'-aminophenyl)-1,4-diazacycloheptane, N,N'-bis-(2-hydroxy-5-aminobenzyl) piperazine, N-(4'-aminophenyl)-p-phenylenediamine and 1,10-bis-(2',5'-diaminophenyl)-1,4,7,10-tetraoxadecane as well as the physiologically acceptable salts thereof.

Most particularly preferred binuclear developer components of formula (E2) are selected from N,N'-bis-(β-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane or one of the physiologically acceptable salts of these compounds.

It is furthermore preferable according to the present specification to use at least one p-aminophenol derivative or one of the physiologically acceptable salts thereof as the developer component. p-Aminophenol derivatives of formula (E3) are particularly preferred

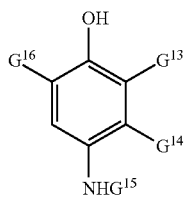
(E3)

in which:
$G^{13}$ denotes a hydrogen atom, a halogen atom, a ($C_1$ to $C_4$)alkyl residue, a ($C_1$ to $C_4$)monohydroxyalkyl residue, a ($C_2$ to $C_4$)polyhydroxyalkyl residue, a ($C_1$ to $C_4$)alkoxy($C_1$ to $C_4$)alkyl residue, a ($C_1$ to $C_4$)aminoalkyl residue, a hydroxy($C_1$ to $C_4$)alkylamino residue, a ($C_1$ to $C_4$) hydroxyalkoxy residue, a ($C_1$ to $C_4$) hydroxyalkyl($C_1$ to $C_4$)aminoalkyl residue or a (di-[($C_1$ to $C_4$)alkyl]amino) ($C_1$ to $C_4$)alkyl residue, and $G^{14}$ denotes a hydrogen or halogen atom, a ($C_1$ to $C_4$)alkyl residue, a ($C_1$ to $C_4$)monohydroxyalkyl residue, a ($C_2$ to $C_4$)polyhydroxyalkyl residue, a ($C_1$ to $C_4$)alkoxy($C_1$ to $C_4$)alkyl residue, a ($C_1$ to $C_4$)aminoalkyl residue or a ($C_1$ to $C_4$)cyanoalkyl residue, $G^{15}$ denotes hydrogen, a ($C_1$ to $C_4$)alkyl residue, a ($C_1$ to $C_4$)monohydroxyalkyl residue, a ($C_2$ to $C_4$)polyhydroxyalkyl residue, a phenyl residue or a benzyl residue, and $G^{16}$ denotes hydrogen or a halogen atom.

The substituents used in formula (E3) are defined according to the present specification in an analogous manner to the above statements.

Preferred p-aminophenols of formula (E3) are in particular p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(β-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl aminomethyl)phenol, 4-amino-2-(α,β-dihydroxyethyl)phenol, 4-amino-2-fluorophenol, 4-amino-2-chlorophenol, 4-amino-2,6-dichlorophenol, 4-amino-2-(diethylaminomethyl)phenol as well as the physiologically acceptable salts thereof.

Most particularly preferred compounds of formula (E3) are p-aminophenol, 4-amino-3-methylphenol, 4-amino-2-aminomethylphenol, 4-amino-2-(α,β-dihydroxyethyl)phenol and 4-amino-2-(diethylaminomethyl)phenol.

The developer component may further be selected from o-aminophenol and derivatives thereof, such as for example 2-amino-4-methylphenol, 2-amino-5-methylphenol or 2-amino-4-chlorophenol.

The developer component may furthermore preferably be selected from heterocyclic developer components, such as for example from pyrimidine derivatives, pyrazole derivatives or the physiologically acceptable salts thereof.

Preferred pyrimidine derivatives are selected according to the present specification from compounds according to formula (E4) or the physiologically acceptable salts thereof,

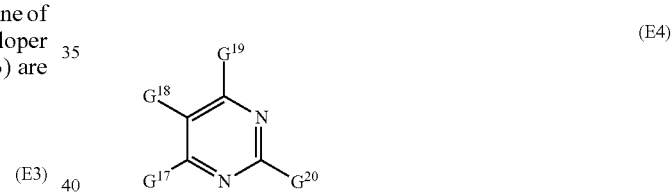
(E4)

in which:
$G^{17}$, $G^{18}$ and $G^{19}$, independently of one another, denote a hydrogen atom, a hydroxyl group, a ($C_1$ to $C_4$)alkoxy group or an amino group, and $G^{20}$ denotes a hydroxyl group or an —$NG^{21}G^{22}$ group, in which $G^{21}$ and $G^{22}$, independently of one another, denote a hydrogen atom, a ($C_1$ to $C_4$)alkyl group, a ($C_1$ to $C_4$)monohydroxyalkyl group, with the proviso that at most two of the groups out of $G^{17}$ $G^{18}$, $G^{19}$ and $G^{20}$ denote a hydroxyl group and at most two of the residues $G^{17}$, $G^{18}$ and $G^{19}$ denote a hydrogen atom. It is in turn preferable if according to formula (E4) at least two groups out of $G^{17}$, $G^{18}$, $G^{19}$ and $G^{20}$ denote an —$NG^{21} G^{22}$ group and at most two groups out of $G^{17}$, $G^{18}$, $G^{19}$ and $G^{20}$ denote a hydroxyl group.

Particularly preferred pyrimidine derivatives are in particular the compounds 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine.

Preferred pyrazole derivatives are selected according to the present specification from compounds according to formula (E5),

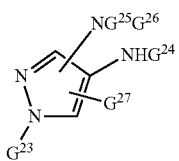 (E5)

in which:
- $G^{23}$, $G^{24}$, $G^{25}$ independently of one another, denote a hydrogen atom, a ($C_1$ to $C_4$)alkyl group, a ($C_1$ to $C_4$)monohydroxyalkyl group, a ($C_2$ to $C_4$)polyhydroxyalkyl group, an optionally substituted aryl group or an optionally substituted aryl($C_1$ to $C_4$)alkyl group, with the proviso that if $G^{25}$ denotes a hydrogen atom, $G^{27}$ in addition to the above groups may also denote an —$NH_2$ group,
- $G^{26}$ denotes a hydrogen atom, a ($C_1$ to $C_4$)alkyl group, a ($C_1$ to $C_4$)monohydroxyalkyl group or a ($C_2$ to $C_4$)polyhydroxyalkyl group, and
- $G^{27}$ denotes a hydrogen atom, an optionally substituted aryl group, a ($C_1$ to $C_4$)alkyl group or a ($C_1$ to $C_4$)monohydroxyalkyl group, in particular a hydrogen atom or a methyl group.

In formula (E5) the residue —$NG^{25}G^{26}$ preferably binds to the 5-position and the residue $G^{27}$ to the 3-position of the pyrazole cycle.

Particularly preferred pyrazole derivatives are in particular the compounds selected from 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(β-aminoethyl)amino-1,3-dimethylpyrazole, as well as the physiologically acceptable salts thereof.

Examples of the residues cited as substituents of the compounds of formulae (E1) to (E5) are listed below: Examples of ($C_1$ to $C_4$)alkyl residues are the groups —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$. Examples according to the present specification of ($C_1$ to $C_4$)alkoxy residues are —$OCH_3$, —$OCH_2CH_3$, —$OCH_2CH_2CH_3$, —$OCH(CH_3)_2$, —$OCH_2CH_2CH_2CH_3$, —$OCH_2CH(CH_3)_2$, —$OCH(CH_3)CH_2CH_3$, —$OC(CH_3)_3$, in particular a methoxy or an ethoxy group.

Preferred examples of a ($C_1$ to $C_4$)monohydroxyalkyl group are furthermore —$CH_2OH$, —$CH_2CH_2OH$, —$CH_2CH_2CH_2OH$, —$CHCH(OH)CH_3$, —$CH_2CH_2CH_2CH_2OH$, the —$CH_2CH_2OH$ group being preferred. A particularly preferred example of a ($C_2$ to $C_4$)polyhydroxyalkyl group is the 1,2-dihydroxyethyl group. Examples of halogen atoms are F, Cl or Br atoms, Cl atoms being most particularly preferred examples. Examples of nitrogen-containing groups are in particular —$NH_2$, ($C_1$ to $C_4$)monoalkylamino groups, ($C_1$ to $C_4$)dialkylamino groups, ($C_1$ to $C_4$)trialkylammonium groups, ($C_1$ to $C_4$)monohydroxyalkyl amino groups, imidazolinium and —$NH_3+$. Examples of ($C_1$ to $C_4$)monoalkylamino groups are —$NHCH_3$, —$NHCH_2CH_3$, —$NHCH_2CH_2CH_3$, —$NHCH(CH_3)_2$.

Examples of ($C_1$ to $C_4$)dialkylamino groups are —$N(CH_3)_2$, —$N(CH_2CH_3)_2$. Examples of ($C_1$ to $C_4$)trialkylammonium groups are —$N^+(CH_3)_3$, —$N^+(CH_3)_2(CH_2CH_3)$, —$N^+(CH_3)(CH_2CH_3)_2$.

Examples of ($C_1$ to $C_4$) hydroxyalkylamino residues are —$NH$—$CH_2CH_2OH$, —$NH$—$CH_2CH_2OH$, —$NH$—$CH_2CH_2CH_2OH$, —$NH$—$CH_2CH_2CH_2OH$. Examples of ($C_1$ to $C_4$)alkoxy($C_1$ to $C_4$)alkyl groups are the groups —$CH_2CH_2$—O—$CH_3$, —$CH_2CH_2CH_2$—O—$CH_3$, —$CH_2CH_2$—O—$CH_2CH_3$, —$CH_2CH_2CH_2$—O—$CH_2CH_3$, —$CH_2CH_2$—O—$CH(CH_3)_2$, —$CH_2CH_2CH_2$—O—$CH(CH_3)_2$.

Examples of hydroxy($C_1$ to $C_4$)alkoxy residues are —O—$CH_2OH$, —O—$CH_2CH_2OH$, —O—$CH_2CH_2CH_2OH$, —O—$CHCH(OH)CH_3$, —O—$CH_2CH_2CH_2CH_2OH$. Examples of ($C_1$ to $C_4$) acetylaminoalkoxy residues are —O—$CH_2NHC(O)CH_3$, —O—$CH_2CH_2NHC(O)CH_3$, —O—$CH_2CH_2CH_2NHC(O)CH_3$, —O—$CH_2CH(NHC(O)CH_3)CH_3$, —O—$CH_2CH_2CH_2CH_2NHC(O)CH_3$. Examples of ($C_1$ to $C_4$) carbamoylaminoalkoxy residues are —O—$CH_2CH_2$—NH—C(O)—$NH_2$, —O—$CH_2CH_2CH_2$—NH—C(O)—$NH_2$, —O—$CH_2CH_2CH_2CH_2$—NH—C(O)—$NH_2$. Examples of ($C_1$ to $C_4$)aminoalkyl residues are —$CH_2NH_2$, —$CH_2CH_2NH_2$, —$CH_2CH_2CH_2NH_2$, —$CH_2CH(NH_2)CH_3$, —$CH_2CH_2CH_2CH_2NH_2$.

Examples of ($C_1$ to $C_4$)cyanoalkyl residues are —$CH_2CN$, —$CH_2CH_2CN$, —$CH_2CH_2CH_2CN$.

Examples of ($C_1$ to $C_4$) hydroxyalkylamino($C_1$ to $C_4$)alkyl residues are —$CH_2CH_2NH$—$CH_2CH_2OH$, —$CH_2CH_2CH_2NH$—$CH_2CH_2OH$, —$CH_2CH_2NH$—$CH_2CH_2CH_2OH$, —$CH_2CH_2CH_2NH$—$CH_2CH_2CH_2OH$.

Examples of di[($C_1$ to $C_4$) hydroxyalkyl]amino($C_1$ to $C_4$)alkyl residues are —$CH_2CH_2N(CH_2CH_2OH)_2$, —$CH_2CH_2CH_2N(CH_2CH_2OH)_2$, —$CH_2CH_2N(CH_2CH_2CH_2OH)_2$, —$CH_2CH_2CH_2N(CH_2CH_2CH_2OH)_2$. An example of aryl groups is the phenyl group. Examples of aryl($C_1$ to $C_4$)alkyl groups are the benzyl group and the 2-phenylethyl group.

Coupler components within the meaning of the present specification permit at least one substitution of a chemical residue of the coupler with the oxidized form of the developer component. A covalent bond forms between the coupler and developer component in this process. Couplers are preferably cyclic compounds bearing at least two functional groups on the at least one ring, selected from (i) optionally substituted amino groups and/or (ii) hydroxyl groups. If the cyclic compound is a six-membered ring (preferably aromatic), said groups are preferably in ortho-position or meta-position to one another.

Coupler components according to the present specification are preferably selected as at least one compound from one of the following classes:
- m-aminophenol and/or derivatives thereof,
- m-diaminobenzene and/or derivatives thereof,
- o-diaminobenzene and/or derivatives thereof,
- o-aminophenol derivatives, such as for example o-aminophenol,
- naphthalene derivatives having at least one hydroxyl group,
- di- or trihydroxybenzene and/or derivatives thereof,
- pyridine derivatives, pyrimidine derivatives,
monohydroxyindole derivatives and/or monoaminoindole derivatives,
monohydroxyindoline derivatives and/or monoaminoindoline derivatives,
pyrazolone derivatives such as for example 1-phenyl-3-methylpyrazol-5-one,
morpholine derivatives such as for example 6-hydroxybenzomorpholine or 6-aminobenzomorpholine,
quinoxaline derivatives such as for example 6-methyl-1,2,3,4-tetrahydroquinoxaline.

Within the context of this example mixtures of two or more compounds from one or more of these classes are likewise in accordance with the present specification.

The m-aminophenols or derivatives thereof for use according to the present specification are preferably selected from at least one compound of formula (K1) and/or from at least one physiologically acceptable salt of a compound according to formula (K1),

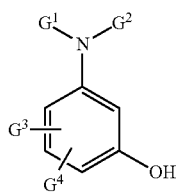

(K1)

in which:
$G^1$ and $G^2$ independently of one another, denote a hydrogen atom, a ($C_1$ to $C_4$)alkyl group, a ($C_3$ to $C_6$)cycloalkyl group, a ($C_2$ to $C_4$)alkenyl group, a ($C_1$ to $C_4$)monohydroxyalkyl group, a ($C_2$ to $C_4$)polyhydroxyalkyl group, a ($C_2$ to $C_4$) perfluoroacyl group, an aryl($C_1$ to $C_6$)alkyl group, an amino($C_1$ to $C_6$)alkyl group, a ($C_1$ to $C_6$)dialkylamino($C_1$ to $C_6$)alkyl group or a ($C_1$ to $C_6$)alkoxy($C_1$ to $C_6$)alkyl group, wherein $G^1$ and $G^2$ together with the nitrogen atom may form a five-membered, six-membered or seven-membered ring,
$G^3$ and $G^4$ independently of one another, denote a hydrogen atom, a halogen atom, a ($C_1$ to $C_4$)alkyl group, a ($C_1$ to $C_4$)alkoxy group, a hydroxyl group, a ($C_1$ to $C_4$)monohydroxyalkyl group, a ($C_2$ to $C_4$)polyhydroxyalkyl group, a hydroxy($C_1$ to $C_4$)alkoxy group, a ($C_1$ to $C_6$)alkoxy($C_2$ to $C_6$)alkoxy group, an aryl group or a heteroaryl group.

Particularly preferred m-aminophenol coupler components are selected from at least one compound from the group which is formed from m-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-diethylaminophenol, N-cyclopentyl-3-aminophenol, 1,3-dihydroxy-5-(methylamino)benzene, 3-ethylamino-4-methylphenol, 2,4-dichloro-3-aminophenol and the physiologically acceptable salts of all aforementioned compounds.

The m-diaminobenzenes or derivatives thereof for use according to the present specification are preferably selected from at least one compound of formula (K2) and/or from at least one physiologically acceptable salt of a compound according to formula (K2),

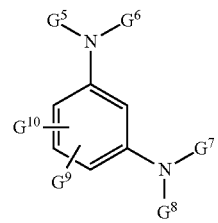

(K2)

in which:
$G^5$, $G^6$, $G^7$ and $G^8$ independently of one another, denote a hydrogen atom, a ($C_1$ to $C_4$)alkyl group, a ($C_3$ to $C_6$)cycloalkyl group, a ($C_2$ to $C_4$)alkenyl group, a ($C_1$ to $C_4$)monohydroxyalkyl group, a ($C_2$ to $C_4$)polyhydroxyalkyl group, a ($C_1$ to $C_4$)alkoxy($C_1$ to $C_4$)alkyl group, an aryl($C_1$ to $C_4$)alkyl group, a heteroaryl($C_1$ to $C_4$)alkyl group, a ($C_2$ to $C_4$) perfluoroacyl group or together with the nitrogen atom form a five-membered or six-membered heterocycle
$G^9$ and $G^{10}$ independently of one another, denote a hydrogen atom, a halogen atom, a ($C_1$ to $C_4$)alkyl group, a ω-(2,4-diaminophenyl) ($C_1$ to $C_4$)alkyl group, a ω-(2,4-diaminophenyloxy) ($C_1$ to $C_4$)alkoxy group, a ($C_1$ to $C_4$)alkoxy group, a hydroxyl group, a ($C_1$ to $C_4$)alkoxy($C_2$ to $C_4$)alkoxy group, an aryl group, a heteroaryl group, a ($C_1$ to $C_4$)monohydroxyalkyl group, a ($C_2$ to $C_4$)polyhydroxyalkyl group, or a hydroxy($C_1$ to $C_4$)alkoxy group.

Particularly preferred m-diaminobenzene coupler components are selected from at least one compound from the group which is formed from m-phenylenediamine, 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2'-hydroxyethyl)aminobenzene and the physiologically acceptable salts of all aforementioned compounds.

The o-diaminobenzenes or derivatives thereof for use according to the present specification are preferably selected from at least one compound of formula (K3) and/or from at least one physiologically acceptable salt of a compound according to formula (K3),

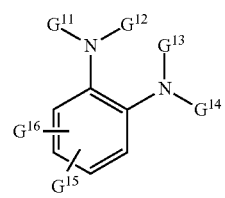

(K3)

in which:
$G^{11}$, $G^{12}$ $G^{13}$ and $G^{14}$ independently of one another, denote a hydrogen atom, a ($C_1$ to $C_4$)alkyl group, a ($C_3$ to $C_6$)cycloalkyl group, a ($C_2$ to $C_4$)alkenyl group, a ($C_1$ to $C_4$)monohydroxyalkyl group, a ($C_2$ to $C_4$)polyhydroxyalkyl group, a ($C_1$ to $C_4$)alkoxy($C_1$ to $C_4$)alkyl group, an aryl($C_1$ to $C_4$)alkyl group, a heteroaryl($C_1$ to $C_4$)alkyl group, a ($C_2$ to $C_4$) perfluoroacyl group or together with the nitrogen atom form a five-membered or six-membered heterocycle $G^{15}$ and $G^{16}$ independently of one another, denote a hydrogen atom, a halogen atom, a carboxyl group, a ($C_1$ to $C_4$)alkyl group, a ($C_1$ to $C_4$)alkoxy group, a hydroxyl group, a ($C_1$ to $C_4$)monohydroxyalkyl group, a ($C_2$ to $C_4$)polyhydroxyalkyl group, or a hydroxy($C_1$ to $C_4$)alkoxy group.

Particularly preferred o-diaminobenzene coupler components are selected from at least one compound from the group formed from 3,4-diaminobenzoic acid and 2,3-diamino-1-methylbenzene and the physiologically acceptable salts of all aforementioned compounds.

Preferred di- or trihydroxybenzenes and derivatives thereof are selected from at least one compound of the group formed from resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene.

The pyridine derivatives for use according to the present specification are preferably selected from at least one compound of formula (K4) and/or from at least one physiologically acceptable salt of a compound according to formula (K4),

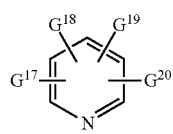

(K4)

in which:
$G^{17}$ and $G^{18}$ independently of one another, denote a hydroxyl group or an —$NG^{21}G^{22}$ group,
  in which $G^{21}$ and $G^{22}$, independently of one another, denote a hydrogen atom, a ($C_1$ to $C_4$)alkyl group, a ($C_3$ to $C_6$)cycloalkyl group, a ($C_2$ to $C_4$)alkenyl group, an aryl group, a ($C_1$ to $C_4$)monohydroxyalkyl group, a ($C_2$ to $C_4$)polyhydroxyalkyl group, a ($C_1$ to $C_4$)alkoxy($C_1$ to $C_4$)alkyl group, an aryl($C_1$ to $C_4$)alkyl group, or a heteroaryl($C_1$ to $C_4$)alkyl group,
$G^{19}$ and $G^{20}$ independently of one another, denote a hydrogen atom, a halogen atom, a ($C_1$ to $C_4$)alkyl group or a ($C_1$ to $C_4$)alkoxy group.

It is preferable if, according to formula (K4), the residues $G^{17}$ and $G^{18}$ are in ortho-position or meta-position to one another.

Particularly preferred pyridine derivatives are selected from at least one compound of the group formed from 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine, and the physiologically acceptable salts of the aforementioned compounds.

Preferred naphthalene derivatives including at least one hydroxyl group are selected from at least one compound of the group which is formed from 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene.

The indole derivatives for use according to the present specification are preferably selected from at least one compound of formula (K5) and/or from at least one physiologically acceptable salt of a compound according to formula (K5),

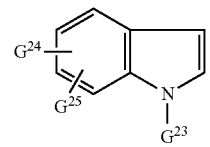

(K5)

in which:
$G^{23}$ denotes a hydrogen atom, a ($C_1$ to $C_4$)alkyl group, a ($C_3$ to $C_6$)cycloalkyl group, a ($C_2$ to $C_4$)alkenyl group, a ($C_1$ to $C_4$)monohydroxyalkyl group, a ($C_2$ to $C_4$)polyhydroxyalkyl group, or an aryl($C_1$ to $C_4$)alkyl group,
$G^{24}$ denotes a hydroxyl group or an —$NO^{26}G^{27}$ group, in which $G^{26}$ and $G^{27}$, independently of one another, denote a hydrogen atom, a ($C_1$ to $C_4$)alkyl group, a ($C_3$ to $C_6$)cycloalkyl group, a ($C_2$ to $C_4$)alkenyl group, a ($C_1$ to $C_4$)monohydroxyalkyl group, or a ($C_2$ to $C_4$)polyhydroxyalkyl group,
$G^{25}$ denotes a hydrogen atom, a halogen atom or a ($C_1$ to $C_4$)alkyl group, with the proviso that $G^{24}$ binds in meta-position or ortho-position to the structural fragment $NG^{23}$ of the formula.

Particularly preferred indole derivatives are selected from at least one compound of the group formed from 4-hydroxyindole, 6-hydroxyindole and 7-hydroxyindole and the physiologically acceptable salts of the aforementioned compounds.

The indoline derivatives for use according to the present specification are preferably selected from at least one compound of formula (K6) and/or from at least one physiologically acceptable salt of a compound according to formula (K6),

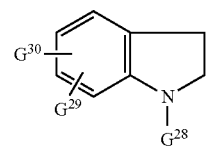

(K6)

in which:
$G^{28}$ denotes a hydrogen atom, a ($C_1$ to $C_4$)alkyl group, a ($C_3$ to $C_6$)cycloalkyl group, a ($C_2$ to $C_4$)alkenyl group, a ($C_1$ to $C_4$)monohydroxyalkyl group, a ($C_2$ to $C_4$)polyhydroxyalkyl group, an aryl($C_1$ to $C_4$)alkyl group,
$G^{29}$ denotes a hydroxyl group or an —$NG^{31}G^{32}$ group, in which $G^{31}$ and $G^{32}$, independently of one another, denote a hydrogen atom, a ($C_1$ to $C_4$)alkyl group, a ($C_3$ to $C_6$)cycloalkyl group, a ($C_2$ to $C_4$)alkenyl group, a ($C_1$ to $C_4$)monohydroxyalkyl group, a ($C_2$ to $C_4$)polyhydroxyalkyl group,
$G^{30}$ denotes a hydrogen atom, a halogen atom or a ($C_1$ to $C_4$)alkyl group, with the proviso that $G^{29}$ binds in meta-position or ortho-position to the structural fragment $NG^{28}$ of the formula.

Particularly preferred indoline derivatives are selected from at least one compound of the group formed from 4-hydroxyindoline, 6-hydroxyindoline and 7-hydroxyindoline and the physiologically acceptable salts of the aforementioned compounds.

Preferred pyrimidine derivatives are selected from at least one compound of the group formed from 4,6-diaminopyrimidine, 4-amino-2,6-dihydroxypyrimidine, 2,4-diamino-6-hydroxypyrimidine, 2,4,6-tri hydroxypyrimidine, 2-amino-4-methylpyrimidine, 2-amino-4-hydroxy-6-methylpyrimidine and 4,6-dihydroxy-2-methylpyrimidine and the physiologically acceptable salts of the aforementioned compounds.

Particularly preferred coupler components according to the present specification are selected from m-aminophenol, 5-amino-2-methylphenol, 3-amino-2-chloro-6-methylphenol, 2-hydroxy-4-aminophenoxyethanol, 5-amino-4-chloro-2-methylphenol, 5-(2'-hydroxyethyl)amino-2-methylphenol, 2,4-dichloro-3-aminophenol, o-aminophenol, m-phenylenediamine, 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2'-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically acceptable salts of the aforementioned compounds.

The coupler components are preferably used in an amount from 0.005 to 20 wt. %, preferably 0.1 to 5 wt. %, relative in each case to the ready-to-use oxidation coloring agent.

Developer components and coupler components may be used in approximately molar amounts to one another. Even if the molar use has proved convenient, a certain excess of individual oxidation dye precursors is not disadvantageous, such that developer components and coupler components may be in a molar ratio of 1:0.5 to 1:3, in particular 1:1 to 1:2.

Examples of the residues cited as substituents of the compounds of formulae (K1) to (K6) are listed below: Examples of ($C_1$ to $C_4$)alkyl residues are the —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$ groups.

Examples according to the present specification of ($C_3$ to $C_6$)cycloalkyl groups are the cyclopropyl, the cyclopentyl and the cyclohexyl group. Examples according to the present specification of ($C_1$ to $C_4$)alkoxy residues are —$OCH_3$, —$OCH_2CH_3$, —$OCH_2CH_2CH_3$, —$OCH(CH_3)_2$, —$OCH_2CH_2CH_2CH_3$, —$OCH_2CH(CH_3)_2$, —$OCH(CH_3)CH_2CH_3$, —$OC(CH_3)_3$, in particular a methoxy or an ethoxy group.

Furthermore, —$CH_2OH$, —$CH_2CH_2OH$, —$CH_2CH_2OH$, —$CH_2CH(OH)CH_3$, —$CH_2CH_2CH_2CH_2OH$ may be cited as preferred examples of a ($C_1$ to $C_4$)monohydroxyalkyl group, the —$CH_2CH_2OH$ group being preferred.

A particularly preferred example of a ($C_2$ to $C_4$)polyhydroxyalkyl group is the 1,2-dihydroxyethyl group. Examples of halogen atoms are F, Cl or Br atoms, Cl atoms being most particularly preferred examples. Examples of nitrogen-containing groups are in particular —$NH_2$, ($C_1$ to $C_4$)monoalkylamino groups, ($C_1$ to $C_4$)dialkylamino groups, ($C_1$ to $C_4$)trialkylammonium groups, ($C_1$ to $C_4$)monohydroxyalkyl amino groups, imidazolinium and —$NH_3+$.

Examples of ($C_1$ to $C_4$)monoalkylamino groups are —$NHCH_3$, —$NHCH_2CH_3$, —$NHCH_2CH_2CH_3$, —$NHCH(CH_3)_2$. Examples of ($C_1$ to $C_4$)dialkylamino groups are —$N(CH_3)_2$, —$N(CH_2CH_3)_2$. Examples of ($C_1$ to $C_4$)alkoxy($C_1$ to $C_4$)alkyl groups are the groups —$CH_2CH_2$—O—$CH_3$, —$CH_2CH_2CH_2$—O—$CH_3$, —$CH_2CH_2$—O—$CH_2CH_3$, —$CH_2CH_2CH_2$—O—$CH_2CH_3$, —$CH_2CH_2$—O—$CH(CH_3)_2$, —$CH_2CH_2CH_2$—O—$CH(CH_3)_2$.

Examples of ($C_1$ to $C_4$)alkoxy($C_1$ to $C_4$)alkoxy groups are the groups —O—$CH_2CH_2$—O—$CH_3$, —O—$CH_2CH_2CH_2$—O—$CH_3$, —O—$CH_2CH_2$—O—$CH_2CH_3$, —O—$CH_2CH_2CH_2$—O—$CH_2CH_3$, —O—$CH_2CH_2$—O—$CH(CH_3)_2$, —O—$CH_2CH_2CH_2$—O—$CH(CH_3)_2$.

Examples of hydroxy($C_1$ to $C_4$)alkoxy residues are —O—$CH_2OH$, —O—$CH_2CH_2OH$, —O—$CH_2CH_2CH_2OH$, —O—$CH_2CH(OH)CH_3$, —O—$CH_2CH_2CH_2CH_2OH$.

Examples of ($C_1$ to $C_4$)aminoalkyl residues are —$CH_2NH_2$, —$CH_2CH_2NH_2$, —$CH_2CH_2CH_2NH_2$, —$CH_2CH(NH_2)CH_3$, —$CH_2CH_2CH_2CH_2NH_2$. An example of aryl groups is the phenyl group, which may also be substituted. Examples of aryl($C_1$ to $C_4$)alkyl groups are the benzyl group and the 2-phenylethyl group.

The agents according to the present specification preferably include as the coloring compound at least one of the following combinations a) to d) of oxidation dye precursors:
a) at least one heterocyclic developer selected from pyrazole derivatives (in particular 1-(2-hydroxyethyl)pyrazole) and pyrimidine derivatives (in particular 2,4,5,6-tetrahydroxypyrimidone), at least one compound selected from m-aminophenol or derivatives thereof as coupler,
b) 4-amino-3-methylphenol, 5-amino-2-methylphenol,
c) p-toluylenediamine, 4-amino-3-methylphenol, 5-amino-2-methylphenol,
d) 2-(β-hydroxyethyl)-p-phenylenediamine, 4-amino-3-methylphenol, 5-amino-2-methylphenol.

The agents according to the present specification may also include at least one substantive dye. These are dyes which attach directly to the hair and require no oxidative process to develop the color. Preferred substantive dyes are nitrophenylene diamines, nitroaminophenols, azo dyes, anthraquinones or indophenols.

Substantive dyes are each preferably used in an amount from 0.001 to 20 wt. %, relative to the total application preparation. The total amount of substantive dyes is preferably at most 20 wt. %.

Substantive dyes may moreover be divided into anionic, cationic and non-ionic substantive dyes.

Preferred anionic substantive dyes are the compounds known under the international names or trade names Tetrabromophenol Blue, Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52.

Preferred cationic substantive dyes are:

(a) cationic triphenylmethane dyes, such as for example Basic Blue 7, Basic Blue 26, Basic Violet 2 and Basic Violet 14,
(b) aromatic systems substituted with a quaternary nitrogen group, such as for example Basic Yellow 57, Basic Red 76, Basic Blue 99, Basic Brown 16 and Basic Brown 17, and
(c) substantive dyes including a heterocyclic compound having at least one quaternary nitrogen atom, such as for example those mentioned in EP-A2-998 908, to which reference is explicitly made here.

Preferred cationic substantive dyes of group (c) are in particular the following compounds:

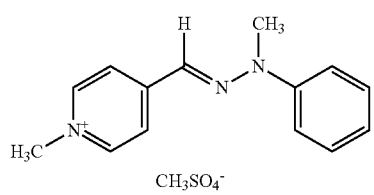
(DZ1)

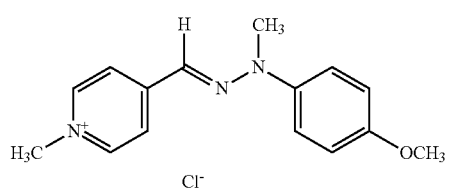
(DZ2)

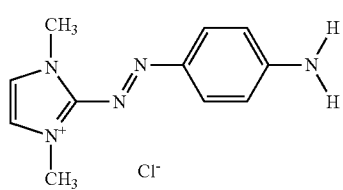
(DZ3)

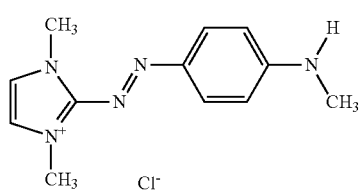
(DZ4)

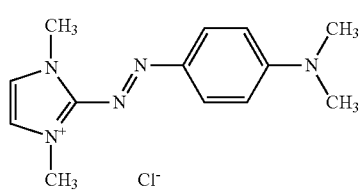
(DZ5)

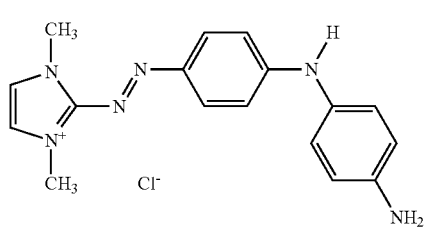
(DZ6)

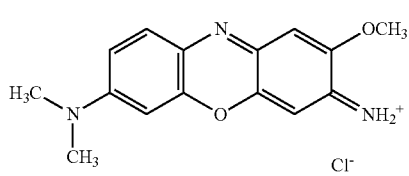
(DZ7)

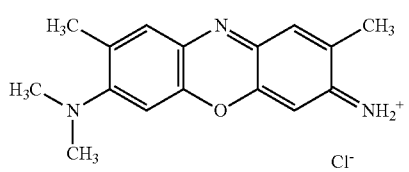
(DZ8)

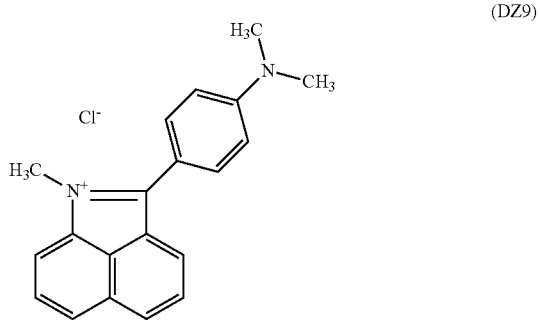
(DZ9)

The compounds of formulae (DZ1), (DZ3) and (DZ5), which are also known under the names Basic Yellow 87, Basic Orange 31 and Basic Red 51, are most particularly preferred cationic substantive dyes of group (c).

The cationic substantive dyes which are sold under the ARIANOR® trademark are likewise most particularly preferred cationic substantive dyes according to the present specification.

Non-ionic substantive dyes: Non-ionic nitro and quinone dyes and neutral azo dyes in particular are suitable as non-ionic substantive dyes.

Preferred non-ionic substantive dyes are the compounds known under the international names or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino] benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-4-nitrophenol.

Naturally occurring dyes, such as are included for example in henna red, henna neutral, henna black, chamomile flowers, sandalwood, black tea, alder buckthorn bark, sage, logwood, madder root, catechu, lotus and alkanet root, may also be used as substantive dyes.

Indoles and indolines including at least two groups selected from hydroxyl and/or amino groups, preferably as a substituent on the six-membered ring, are preferably used as coloring compounds of the precursors of nature-analogous dyes. These groups may bear further substituents, for example in the form of an etherification or esterification of the hydroxyl group or an alkylation of the amino group. In a further example the coloring agents include at least one indole and/or indoline derivative. Compositions according to the present specification including precursors of nature-analogous dyes are preferably used as air-oxidative coloring agents. In this example said compositions are accordingly not mixed with an additional oxidizing agent.

Derivatives of 5,6-dihydroxyindoline of formula (RN1) are particularly suitable as precursors of nature-analogous hair dyes,

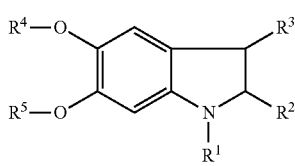

(RN1)

in which, independently of one another,
- $R^1$ denotes hydrogen, a $C_1$-$C_4$ alkyl group or a $C_1$-$C_4$ hydroxyalkyl group,
- $R^2$ denotes hydrogen or a —COOH group, in which the —COOH group may also be present as a salt with a physiologically acceptable cation,
- $R^3$ denotes hydrogen or a $C_1$-$C_4$ alkyl group,
- $R^4$ denotes hydrogen, a $C_1$-$C_4$ alkyl group or a —CO—$R^6$ group, in which $R^6$ denotes a $C_1$-$C_4$ alkyl group, and
- $R^5$ denotes one of the groups cited under $R^4$, as well as physiologically acceptable salts of these compounds with an organic or inorganic acid.

Particularly preferred derivatives of indoline are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline and 5,6-dihydroxyindoline-2-carboxylic acid.

Within this group, particular emphasis is given to N-methyl-5,6-dihydroxyindoline, N-ethyl-5,6-dihydroxyindoline, N-propyl-5,6-dihydroxyindoline, N-butyl-5,6-dihydroxyindoline and in particular 5,6-dihydroxyindoline.

Derivatives of 5,6-dihydroxyindole of formula (RN2) are moreover outstandingly suitable as precursors of nature-analogous hair dyes,

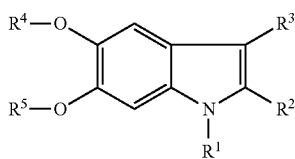

(RN2)

in which, independently of one another,
- $R^1$ denotes hydrogen, a $C_1$-$C_4$ alkyl group or a $C_1$-$C_4$ hydroxyalkyl group,
- $R^2$ denotes hydrogen or a —COOH group, in which the —COOH group may also be present as a salt with a physiologically acceptable cation,
- $R^3$ denotes hydrogen or a $C_1$-$C_4$ alkyl group,
- $R^4$ denotes hydrogen, a $C_1$-$C_4$ alkyl group or a —CO—$R^6$ group, in which $R^6$ denotes a $C_1$-$C_4$ alkyl group, and
- $R^5$ denotes one of the groups cited under $R^4$, as well as physiologically acceptable salts of these compounds with an organic or inorganic acid.

Particularly preferred indole derivatives are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid.

Within this group, particular emphasis is given to N-methyl-5,6-dihydroxyindole, N-ethyl-5,6-dihydroxyindole, N-propyl-5,6-dihydroxyindole, N-butyl-5,6-dihydroxyindole and in particular 5,6-dihydroxyindole.

The indoline and indole derivatives may be used both as free bases and in the form of their physiologically acceptable salts with inorganic or organic acids, for example hydrochlorides, sulfates and hydrobromides.

Most particularly preferred cosmetic agents according to the present specification obey at least one of the following examples (A) to (F):

(A): A cosmetic agent for coloring keratin-containing fibers, in particular human hair, comprising in a cosmetically acceptable, hydrous carrier:

(a) at least one water-soluble, polyether-modified compound of general formula (PE-1)

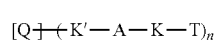

(PE-1)

in which:
- A denotes a polyoxyalkylene chain consisting of either ethylene oxide units or both ethylene oxide and propylene oxide units, wherein the polyoxyalkylene chain has a maximum proportion of 50 wt. % of propylene oxide units, relative to the weight of A,
- K and K' independently of one another, denote a connectivity selected from a covalent bond or from a molecular fragment having two free valences,
- T denotes a residue

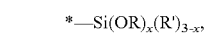

in which R and R', independently of one another, denote a ($C_1$ to $C_4$)alkyl group (preferably methyl or ethyl), x denotes 1, 2 or 3,

- Q denotes an organic structural fragment derived from linear, branched, cyclic or heterocyclic hydrocarbons, all of which may each be saturated, unsaturated or aromatic,
- n denotes an integer from 3 to 64 (in particular 3, 4, 5, 6, 7 or 8)

and (b) at least one polar alkoxysilane of formula (SI-1)

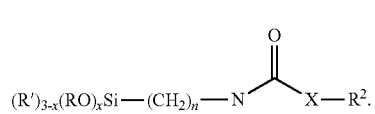

(SI-1)

in which:
- R and R' independently of one another, denote a ($C_1$ to $C_4$)alkyl group (preferably methyl or ethyl),
- x denotes 1, 2 or 3,
- n denotes 1, 2 or 3,
- X denotes an oxygen atom or an NH group,
- $R^2$ denotes a *—$(CH_2)_m$—$N^+R^3R^4R^5$ group in which:
m denotes 2, 3, 4, 5 or 6,
$R^3$, $R^4$ and $R^5$, independently of one another, denote ($C_1$ to $C_{20}$)alkyl, ($C_8$ to $C_{20}$) acyloxy($C_2$ to $C_3$)alkyl, ($C_2$ to $C_{20}$)alkenyl, ($C_8$ to $C_{20}$)alkanamido($C_2$ to $C_3$)alkyl or aryl($C_1$ to $C_4$)alkyl,
and
(c) at least one coloring compound.

(B): A cosmetic agent for coloring keratin-containing fibers, in particular human hair, comprising in a cosmetically acceptable, hydrous carrier relative in each case to the weight of the agent:
(a) 0.01 to 15.0 wt. %, particularly preferably from 0.1 to 8.0 wt. %, most particularly preferably 0.2 to 5.0 wt. %, most preferably from 0.25 to 2.5 wt. %, of at least one water-soluble, polyether-modified compound of general formula (PE-1)

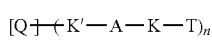
(PE-1)

in which:
A denotes a polyoxyalkylene chain consisting of either ethylene oxide units or both ethylene oxide and propylene oxide units, wherein the polyoxyalkylene chain has a maximum proportion of 50 wt. % of propylene oxide units, relative to the weight of A,
K and K' independently of one another, denote a connectivity selected from a covalent bond or from a molecular fragment having two free valences,
T denotes a residue

, in which R and R', independently of one another, denote a ($C_1$ to $C_4$)alkyl group (in particular methyl or ethyl), x denotes 1, 2 or 3,
Q denotes an organic structural fragment derived from linear, branched, cyclic or heterocyclic hydrocarbons, all of which may each be saturated, unsaturated or aromatic,
n denotes an integer from 3 to 64 (in particular 3, 4, 5, 6, 7 or 8)
and
(b) 0.01 to 15.0 wt. %. particularly preferably from 0.1 to 8.0 wt. %, most particularly preferably 0.2 to 5.0 wt. %, most preferably from 0.25 to 2.5 wt. %, of at least one polar alkoxysilane of formula (SI-1)

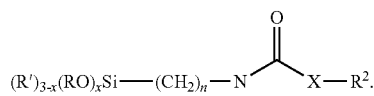
(SI-1)

in which:
R and R' independently of one another, denote a ($C_1$ to $C_4$)alkyl group (preferably methyl or ethyl),
x denotes 1, 2 or 3,
n denotes 1, 2 or 3,
X denotes an oxygen atom or an NH group,
$R^2$ denotes a *—$(CH_2)_m$—$N^+R^3R^4R^5$ group in which:
m denotes 2, 3, 4, 5 or 6,
$R^3$, $R^4$ and $R^5$, independently of one another, denote ($C_1$ to $C_{20}$)alkyl, ($C_8$ to $C_{20}$) acyloxy($C_2$ to $C_3$)alkyl, ($C_2$ to $C_{20}$)alkenyl, ($C_8$ to $C_{20}$)alkanamido($C_2$ to $C_3$)alkyl or aryl($C_1$ to $C_4$)alkyl,
and
(c) at least one coloring compound.

(C): A cosmetic agent for coloring keratin-containing fibers, in particular human hair, comprising in a cosmetically acceptable, hydrous carrier:
(a) at least one water-soluble, polyether-modified compound of general formula (PE-1)

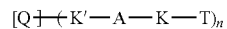
(PE-1)

in which:
A denotes a polyoxyalkylene chain consisting of either ethylene oxide units or both ethylene oxide and propylene oxide units, wherein the polyoxyalkylene chain has a maximum proportion of 50 wt. % of propylene oxide units, relative to the weight of A,
K and K' independently of one another, denote a connectivity selected from a covalent bond or from a molecular fragment having two free valences,
T denotes a residue

, in which R and R', independently of one another, denote a ($C_1$ to $C_4$)alkyl group (preferably methyl or ethyl), x denotes 1, 2 or 3,
Q is an organic structural fragment derived from glycerol, monosaccharide or disaccharide,
n denotes an integer from 3 to 64 (in particular 3, 4, 5, 6, 7 or 8)
and
(b) at least one polar alkoxysilane of formula (SI)

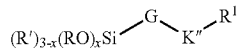
(SI)

in which:
G denotes a ($C_1$ to $C_3$)alkylene group,
K" denotes a connectivity selected from a covalent bond or from a molecular fragment having two free valences,
$R^1$ denotes a molecular fragment comprising at least one polar substituent selected from at least one representative of the group consisting of quaternized nitrogen atoms, amino groups, anionic residues,
x denotes 1, 2 or 3,
R and R' independently of one another, denote a ($C_1$ to $C_4$)alkyl group (preferably methyl or ethyl),
and
(c) at least one coloring compound.

(D): A cosmetic agent for coloring keratin-containing fibers, in particular human hair, comprising in a cosmetically acceptable, hydrous carrier:
(a) at least one water-soluble, polyether-modified compound of general formula (PE-1)

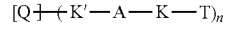
(PE-1)

in which:
A denotes a polyoxyalkylene chain consisting of either ethylene oxide units or both ethylene oxide and propylene oxide units, wherein the polyoxyalkylene chain has a maximum proportion of 50 wt. % of propylene oxide units, relative to the weight of A, K and K' independently of one another, denote a connectivity selected from a covalent bond or from a molecular fragment having two free valences, T denotes a residue

*—Si(OR)$_x$(R')$_{3-x}$, in which R and R', independently of one another, denote a (C$_1$ to C$_4$)alkyl group (in particular methyl or ethyl), x denotes 1, 2 or 3, Q is an organic structural fragment derived from glycerol, monosaccharide or disaccharide, n denotes an integer from 3 to 64 (in particular 3, 4, 5, 6, 7 or 8)

and (b) at least one polar alkoxysilane of formula (SI-1)

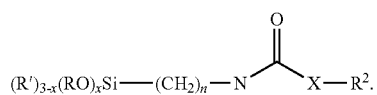
(SI-1)

in which:

R and R' independently of one another, denote a (C$_1$ to C$_4$)alkyl group (preferably methyl or ethyl), x denotes 1, 2 or 3, n denotes 1, 2 or 3, X denotes an oxygen atom or an NH group, R$^2$ denotes a *—(CH$_2$)$_m$—N$^+$R$^3$R$^4$R$^5$ group in which:

m denotes 2, 3, 4, 5 or 6,

R$^3$, R$^4$ and R$^5$, independently of one another, denote (C$_1$ to C$_{20}$)alkyl, (C$_8$ to C$_{20}$) acyloxy(C$_2$ to C$_3$)alkyl, (C$_2$ to C$_{20}$)alkenyl, (C$_8$ to C$_{20}$)alkanamido(C$_2$ to C$_3$)alkyl or aryl(C$_1$ to C$_4$)alkyl, and (c) at least one coloring compound.

(E): A cosmetic agent for coloring keratin-containing fibers, in particular human hair, comprising in a cosmetically acceptable, hydrous carrier relative in each case to the weight of the agent:

(a) 0.01 to 15.0 wt. %, particularly preferably from 0.1 to 8.0 wt. %, most particularly preferably 0.2 to 5.0 wt. %, most preferably from 0.25 to 2.5 wt. %, of at least one water-soluble, polyether-modified compound of general formula (PE-1)

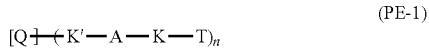
(PE-1)

in which:

A denotes a polyoxyalkylene chain consisting of either ethylene oxide units or both ethylene oxide and propylene oxide units, wherein the polyoxyalkylene chain has a maximum proportion of 50 wt. % of propylene oxide units, relative to the weight of A, K and K' independently of one another, denote a connectivity selected from a covalent bond or from a molecular fragment having two free valences, T denotes a residue

*—Si(OR)$_x$(R')$_{3-x}$, in which R and R', independently of one another, denote a (C$_1$ to C$_4$)alkyl group (in particular methyl or ethyl), x denotes 1, 2 or 3, Q is an organic structural fragment derived from glycerol, monosaccharide or disaccharide, n denotes an integer from 3 to 64 (in particular 3, 4, 5, 6, 7 or 8)

and (b) 0.01 to 15.0 wt. %. particularly preferably from 0.1 to 8.0 wt. %, most particularly preferably 0.2 to 5.0 wt. %, most preferably from 0.25 to 2.5 wt. %, of at least one polar alkoxysilane of formula (SI-1)

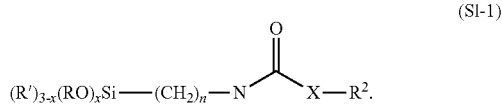
(SI-1)

in which:

R and R' independently of one another, denote a (C$_1$ to C$_4$)alkyl group (in particular methyl or ethyl), x denotes 1, 2 or 3, n denotes 1, 2 or 3, X denotes an oxygen atom or an NH group, R$^2$ denotes a *—(CH$_2$)$_m$—N$^+$R$^3$R$^4$R$^5$ group in which:

m denotes 2, 3, 4, 5 or 6,

R$^3$, R$^4$ and R$^5$, independently of one another, denote (C$_1$ to C$_{20}$)alkyl, (C$_8$ to C$_{20}$) acyloxy(C$_2$ to C$_3$)alkyl, (C$_2$ to C$_{20}$)alkenyl, (C$_8$ to C$_{20}$)alkanamido(C$_2$ to C$_3$)alkyl or aryl(C$_1$ to C$_4$)alkyl, and (c) at least one coloring compound.

(F): A cosmetic agent for coloring keratin-containing fibers, in particular human hair, comprising in a cosmetically acceptable, hydrous carrier relative in each case to the weight of the agent:

(a) 0.01 to 15.0 wt. %, particularly preferably from 0.1 to 8.0 wt. %, most particularly preferably 0.2 to 5.0 wt. %, most preferably from 0.25 to 2.5 wt. %, of at least one water-soluble, polyether-modified compound of general formula (PE-1)

(PE-1)

in which:

A denotes a polyoxyalkylene chain consisting of either ethylene oxide units or both ethylene oxide and propylene oxide units, wherein the polyoxyalkylene chain has a maximum proportion of 50 wt. % of propylene oxide units, relative to the weight of A, K and K' independently of one another, denote a connectivity selected from a covalent bond or from a molecular fragment having two free valences, T denotes a residue

*—Si(OR)$_x$(R')$_{3-x}$, in which R and R', independently of one another, denote a (C$_1$ to C$_4$)alkyl group (preferably methyl or ethyl), x denotes 1, 2 or 3, Q is an organic structural fragment derived from glycerol, monosaccharide or disaccharide, n denotes an integer from 3 to 64 (in particular 3, 4, 5, 6, 7 or 8)

and
(b) 0.01 to 15.0 wt. %. particularly preferably from 0.1 to 8.0 wt. %, most particularly preferably 0.2 to 5.0 wt. %, most preferably from 0.25 to 2.5 wt. %, of at least one polar alkoxysilane of formula (SI)

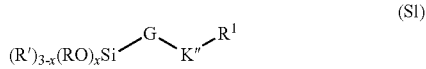

in which:
G denotes a ($C_1$ to $C_3$)alkylene group,
K″ denotes a connectivity selected from a covalent bond or from a molecular fragment having two free valences,
$R^1$ denotes a molecular fragment comprising at least one polar substituent selected from at least one representative of the group consisting of quaternized nitrogen atoms, amino groups, and anionic residues,
x denotes 1, 2 or 3,
R and R' independently of one another, denote a ($C_1$ to $C_4$)alkyl group (preferably methyl or ethyl),
and
(c) at least one coloring compound.

Examples (A) to (F) of the cosmetic agent according to the present specification preferably include as the coloring component preferably at least one oxidation dye precursor of the developer component type and optionally additionally at least one coupler component.

Within the context of examples (A) to (F) the features of components (a) and (b) according to the present specification of the active agent combination identified in each case as being preferred, in particular the proportions of components (a) and (b) previously specified as being preferred, naturally apply with the necessary changes.

The active agent combination used according to the present specification develops its effect particularly in agents for the oxidative coloring of keratin-containing fibers, in particular human hair. It has therefore proved preferable to use an agent according to the present specification for the oxidative coloring of keratin-containing fibers which comprises in a cosmetic carrier:
(a) at least one water-soluble polymer comprising at least one *—Si(OR)$_x$(R')$_{3-x}$ residue, in which R and R', independently of one another, denote a ($C_1$ to $C_4$)alkyl group (preferably methyl or ethyl), x denotes 1, 2 or 3,
and
(b) at least one polar alkoxysilane compound of formula (SI)

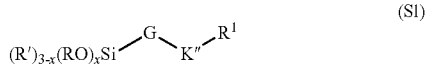

in which:
G denotes a ($C_1$ to $C_3$)alkylene group,
K″ denotes a connectivity selected from a covalent bond or from a molecular fragment having two free valences,
$R^1$ denotes a molecular fragment comprising at least one polar substituent selected from at least one representative of the group consisting of quaternized nitrogen atoms, amino groups, and anionic residues,
x denotes 1, 2 or 3,
R and R' independently of one another, denote a ($C_1$ to $C_4$)alkyl group (in particular methyl or ethyl), and
(c) at least one oxidation dye precursor of the developer component type and optionally additionally at least one coupler component as the coloring compound,
and
(d) at least one oxidizing agent.

The aforementioned preferred features (see above) apply in each case to (a) and (b) and (c).

It is particularly preferable according to the present specification to add to the agents according to the present specification (A) to (F) as the coloring compound (c) at least one oxidation dye precursor of the developer component type and optionally additionally at least one coupler component and additionally (d) at least one oxidizing agent.

The oxidizing agents within the meaning of the agent differ from atmospheric oxygen and have an oxidizing potential such that they may oxidize an oxidation dye precursor of the developer type. Hydrogen peroxide and/or at least one addition product thereof, in particular with inorganic or organic compounds, such as for example sodium perborate, sodium percarbonate, magnesium percarbonate, sodium percarbamide, polyvinylpyrrolidone.n $H_2O_2$ (n is a positive integer greater than 0), urea peroxide and melamine peroxide, is preferably suitable as the oxidizing agent.

The oxidizing agent is preferably included in the cosmetic agent in an amount from 1.0 to 10 wt. %, in particular 3.0 to 10.0 wt. %, relative in each case to the weight of the ready-to-use cosmetic coloring agent.

In a preferred example of the present specification the cosmetic coloring agent according to the present specification is mixed prior to application from a first composition including in a cosmetic carrier at least one color-changing component and a second composition including in a cosmetic carrier at least one oxidizing agent, with the proviso that the first composition and/or the second composition includes at least one said active agent combination of the first subject matter of the present specification. The first and second compositions are packaged separately from one another each in their own compartment and provided together in the form of a packaging unit (kit). Shortly before application the two components are mixed together. The resulting ready-to-use coloring preparation preferably has a pH in the range from 6 to 12, in particular from pH 7.5 to 10.

The cosmetic coloring agent according to the present specification preferably includes at least one alkalizing agent. The alkalizing agents for use according to the present specification are preferably selected from at least one representative of the group formed from ammonia, basic amino acids, alkali hydroxides, alkanolamines, alkali metal metasilicates, urea, alkali phosphates and alkali hydrogen phosphates. Preferred alkali metal ions are lithium, sodium, potassium, in particular sodium or potassium. The alkalizing agents are moreover preferably different from ammonia.

The basic amino acids which may be used as alkalizing agents according to the present specification are preferably selected from the group formed from L-arginine, D-arginine, D,L-arginine, L-histidine, D-histidine, D,L-histidine, L-lysine, D-lysine, D,L-lysine; L-arginine, D-arginine, D,L-arginine are particularly preferably used as an alkalizing agent within the meaning of the present specification.

The alkali hydroxides which may be used as the alkalizing agent according to the present specification are preferably selected from the group formed from sodium hydroxide and potassium hydroxide.

The alkanolamines which may be used as the alkalizing agent according to the present specification are preferably selected from primary amines having a $C_2$-$C_6$ alkyl parent substance bearing at least one hydroxyl group. Particularly preferred alkanolamines are selected from the group formed from 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol. Most particularly preferred alkanolamines according to the present specification are selected from the group including 2-aminoethan-1-ol, 2-amino-2-methylpropan-1-ol and 2-amino-2-methylpropane-1,3-diol.

The alkalizing agent is particularly preferably selected from at least one compound from the group formed from 2-aminoethanol, 2-amino-2-methylpropan-1-ol, 2-amino-2-methylpropane-1,3-diol, potassium hydroxide, L-arginine, D-arginine, D,L-arginine, N-methyl glucamine and urea.

The coloring agents according to the present specification may moreover include further active agents, auxiliary substances and additives, such as for example non-ionic polymers; cationic polymers; zwitterionic and amphoteric polymers; anionic polymers such as for example polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methylvinyl ether/maleic anhydride copolymers and acrylic acid/ethyl acrylate/N-tert-butyl acrylamide terpolymers; hair-conditioning compounds such as phospholipids; protein hydrolysates, in particular elastin, collagen, keratin, milk protein, soy protein and wheat protein hydrolysates, condensation products thereof with fatty acids and quaternized protein hydrolysates; perfume oils, dimethyl isosorbide and cyclodextrins; active agents to improve the fiber structure, in particular mono-, di- and oligosaccharides, such as for example glucose, galactose, fructose, fruit sugars and lactose; cationic surfactants; defoaming agents; anti-dandruff active agents; light stabilizers, in particular derivatized benzophenones, cinnamic acid derivatives and triazines; active agents such as allantoin, pyrrolidone carboxylic acids and salts thereof as well as bisabolol; vitamins, provitamins and vitamin precursors, in particular those from groups A, $B_3$, $B_5$, $B_6$, C, E, F and H; plant extracts, in particular extracts from green tea, oak bark, stinging nettle, witch hazel, hops, chamomile, burdock, horsetail, whitethorn, lime blossom, almond, aloe vera, pine, horse chestnut, sandalwood, juniper, coconut, mango, apricot, lemon, wheat, kiwi, melon, orange, grapefruit, sage, rosemary, birch, mallow, lady's smock, wild thyme, yarrow, thyme, melissa, restharrow, coltsfoot, marshmallow, meristem, ginseng or ginger root; cholesterol; consistency modifiers; fats and waxes; complexing agents; swelling and penetrating substances; opacifiers; pearlescent agents; solid pigments; stabilizing agents for hydrogen peroxide and other oxidizing agents; propellants; antioxidants.

The cosmetic agents according to the present specification may include at least one compound selected from organic amines comprising 2 to 20 carbon atoms, carboxylate complex compounds of tin, alkoxide compounds of tin, carboxylate complex compounds of lead, organoaluminum compounds, metal complexes of organic dicarbonyl compounds and metal complexes of organic dicarboxylic acid esters.

The preferred examples of the first subject matter of the present specification apply with the necessary changes to the second subject matter of the present specification.

The present specification thirdly provides a cosmetic method in which an active agent combination of:
(a) at least one water-soluble polymer comprising at least one *—Si(OR)$_x$(R')$_{3-x}$ residue, in which R and R', independently of one another, denote a ($C_1$ to $C_4$)alkyl group (preferably methyl or ethyl), x denotes 1, 2 or 3, and
(b) at least one polar alkoxysilane compound of formula (SI)

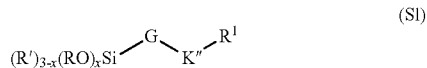

in which:
G denotes a ($C_1$ to $C_3$)alkylene group,
K" denotes a connectivity selected from a covalent bond or from a molecular fragment having two free valences,
$R^1$ denotes a molecular fragment comprising at least one polar substituent selected from at least one representative of the group consisting of quaternized nitrogen atoms, amino groups and anionic residues
x denotes 1, 2 or 3,
R and R' independently of one another, denote a ($C_1$ to $C_4$)alkyl group (in particular methyl or ethyl),
acts on keratin-containing fibers (in particular human hair) synthetically colored with at least one coloring compound and after a contact time is rinsed off again. A preferred example of this method according to the present specification is a method for coloring keratin-containing fibers in which an agent of the second subject matter of the present specification is applied to the fibers and is rinsed off again after a contact time.

The application temperatures may be in a range between 15 and 40° C. After a contact time of generally 5 to 45 minutes the hair coloring agent is removed by rinsing the hair that is to be colored. There is no need to wash with a shampoo afterwards if a highly surfactant-containing carrier, e.g. a coloring shampoo, was used.

The preferred examples of the first and second subject matter of the present specification apply with the necessary changes to the third subject matter of the present specification.

Examples

The examples that follow indicate agents that were produced according to the present specification for the treatment of keratinous fibers. Unless otherwise indicated, all values in the following examples are given as weight percent.

The molecular weights given in the examples section are number-average molecular weights of the starting compounds (polyether polyols) used to produce the prepolymers. The number-average molecular weight of the polyols may be determined by calculation from the functionality of the compounds or the functionality of the mixture components and the OH number of the compound or the mixture (determined in accordance with Deutsches Institut fur Normung E.V. (DIN) 53240) using end-group analysis. If different compounds are used in place of the polyols as starting compounds, their number-average molecular weight is important. Thus, for example, the number-average molecular weight of amines may be determined by end-group analysis with potentiometric titration in accordance with DIN 16945.

Production of suitable water-soluble polymers:

Synthesis Example 1

Three-Arm Triethoxysilyl-Terminated Polyether (PP1)

The polyether polyol that is used is a three-arm random poly(ethylene oxide co-propylene oxide) based on glycerol (see formula (PE-1f) above) having an EO/PO ratio of 80/20 and having a number-average molecular weight of approx. 5000 g/mol, obtained from DOW Chemicals (Voranol® CP 1421). Before the reaction the polyol was heated under vacuum for 1 h at 80° C. with stirring.

(3-Isocyanatopropyl)triethoxysilane (317 mg, 1.0 eq.) was added slowly to the dried polyether polyol (2.04 g, 0.41 mmol). The reaction mixture was stirred for a further 2 days at 100° C. under protective gas until the vibration band for the NCO group disappeared in IR measurement. A product is obtained in which there is a triethoxysilyl group present at each of the free ends of the polymer arms of the star-shaped prepolymer. The product is a colorless, viscous liquid.

Coloring Examples

Relative to the total weight of the mixture, 0.5 wt. % of a water-soluble polymer PP1 in combination with 0.5 wt. % of a polar alkoxysilane consisting of
SIa=3-aminopropyltriethoxysilane
SIb=silane of formula (SI-1c) (R denotes a linear $C_{16}$ acyl group and $R^3$ denotes methyl)
were incorporated into the coloring cream of the commercial product Igora Royal® 6-88 (Schwarzkopf). Immediately before being applied to hair strands (1 g of standardized "European natural hair 6/0" batch no. 06/2010, N93 from Kerling International, Germany, glued to the hair bundle at one end), the resulting modified coloring cream was mixed with a commercial 6 wt. % hydrogen peroxide-containing developer dispersion Oxigenta® (Schwarzkopf) in the weight ratio 1 to 1 to form a hair coloring agent according to the present specification.

The ready-to-use coloring agent was then applied to a hair strand in the weight ratio 4 g of coloring agent to 1 g of hair, left to act for 30 minutes at 32° C. and then rinsed from the fiber. A total of 4 hair strands were colored in this way. Furthermore, 4 hair strands were colored in accordance with the above procedure using the above commercial product without the addition of said polymer PP1/silane combination (not according to the present specification).

The strands were allowed to dry in each case and measured by colorimetry to determine the L,a,b starting values for each strand (Spectraflash 450 device, Colortools software). Eight measuring points were taken for each hair strand, and for each value of the strands colored according to the present specification in one group and the strands colored not according to the present specification in another group the arithmetic mean for the group was calculated to obtain the $L_0, a_0, b_0$ values in each case. Exactly the same procedure was used for the following colorimetric measurements.

To determine the wash fastness the hair strands were subjected to a washing procedure that simulates hair washing: an ultrasonic bath was filled with aqueous shampoo solution (2 wt. % of Schauma "7 Kräuter" shampoo). The colored hair strands were immersed in this washing solution and then treated for 15 min with ultrasound (level 5). This treatment corresponds to the cleaning performance of six hair washes. Then the strands were rinsed thoroughly, dried and measured again by colorimetry. The strands were then subjected to a further washing cycle. The wash fastness was assessed from the calculation of the color difference of the strands before washing and after each washing cycle and determined as follows:

$$\Delta E = [(L_i - L_0)^2 + (a_i - a_0)^2 + (b_i - b_0)^2]^{1/2}$$

$L_i, a_i, b_i$ Values after 6, 12, 18, 24 and 36 hair washes
$L_0, a_0, b_0$ Values after 0 hair washes per hair strand

TABLE 1

| ΔE after 6, 12, 18, 24 and 30 washes | | | | | |
|---|---|---|---|---|---|
| | Number of washes | | | | |
| | 6 | 12 | 18 | 24 | 30 |
| Commercial product | 2.8 | 3.4 | 4.8 | 5.9 | 7.1 |
| Agent according to the present specification with PP1/SIa | 2.1 | 3.3 | 3.9 | 4.6 | 5.8 |
| Agent according to the present specification with PP1/SIb | 2.1 | 3.0 | 3.6 | 3.9 | 4.5 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of the elements described in an exemplary embodiment without departing from the scope of the invention as set forth in the appended claims and their legal equivalents.

The invention claimed is:

1. A method to improve synthetic colorings of coloring compounds on keratin-containing fibers, the method comprising applying an active agent combination comprising:
   (a) at least one water-soluble polymer comprising at least one *—Si(OR)$_x$(R')$_{3-x}$ residue, in which R and R', independently of one another, denote a ($C_1$ to $C_4$) alkyl group and x denotes 1, 2 or 3;
   (b) at least one polar alkoxysilane compound of formula (SI)

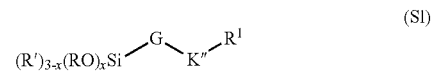

in which:
G denotes a ($C_1$ to $C_3$) alkylene group,
K" denotes a connectivity selected from a covalent bond or from a molecular fragment having two free valences,
$R^1$ denotes a molecular fragment comprising at least one polar substituent selected from the group consisting of quaternized nitrogen atoms, amino groups, anionic residues, or combinations thereof,
x denotes 1, 2 or 3,
R and R' independently of one another, denote a ($C_1$ to $C_4$) alkyl group; and
   (c) at least one coloring compound to color the keratin-containing fibers; and
rinsing off the active agent combination.

2. A cosmetic agent for coloring keratin-containing fibers, comprising, in a cosmetic carrier:
   (a) at least one water-soluble polymer comprising at least one *—Si(OR)$_x$(R')$_{3-x}$ residue, in which R and R', independently of one another, denote a ($C_1$ to $C_4$) alkyl group and x denotes 1, 2 or 3;
   (b) at least one polar alkoxysilane compound of formula (SI)

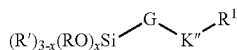 (SI)

in which:
G denotes a ($C_1$ to $C_3$) alkylene group,
K" denotes a connectivity selected from a covalent bond or from a molecular fragment having two free valences,
$R^1$ denotes a molecular fragment comprising at least one polar substituent selected from the group consisting of quaternized nitrogen atoms, amino groups, anionic residues, or combinations thereof,
x denotes 1, 2 or 3,
R and R' independently of one another, denote a ($C_1$ to $C_4$) alkyl group; and
(c) at least one coloring compound to color the keratin-containing fibers, in which the at least one coloring compound comprises at least one of:
 (i) an oxidative dye precursor of a developer component type;
 (ii) a substantive dye; and
 (iii) a precursor of a nature-analogous dye;
in which the change in color of the keratin fibers that results from the treatment of the keratin fibers with the agent persists through the first shampoo of the keratin fibers following treatment with the agent.

3. The cosmetic agent of claim 2, wherein said at least one water-soluble polymer comprises a water-soluble, polyether-modified organic polymer, which has at least one polyether structural unit, wherein said polyether structural unit
 (i) comprises a polyoxyalkylene chain selected from the group consisting of ethylene oxide units, and the combination of ethylene oxide and propylene oxide units, wherein the polyoxyalkylene chain has a maximum proportion of 50 wt. % of propylene oxide units, relative to the weight of the polyoxyalkylene chain, and
 (ii) has at least one *—$Si(OR)_x(R')_{3-x}$ residue, in which R and R', independently of one another, denote a ($C_1$ to $C_4$) alkyl group and x denotes 1, 2 or 3.

4. The cosmetic agent of claim 2, wherein said at least one water-soluble polymer comprises a compound of general formula (PE-1)

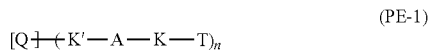 (PE-1)

in which:
A denotes a polyoxyalkylene chain selected from the group consisting of ethylene oxide units, and the combination of ethylene oxide and propylene oxide units, wherein the polyoxyalkylene chain has a maximum proportion of 50 wt. % of propylene oxide units, relative to the weight of A,
K and K' independently of one another, denote a connectivity selected from a covalent bond or from a molecular fragment having two free valences,
T denotes a residue *—$Si(OR)_x(R')_{3-x}$, in which R and R', independently of one another, denote a ($C_1$ to $C_4$) alkyl group and x denotes 1, 2 or 3,
Q denotes an organic structural fragment derived from linear, branched, cyclic or heterocyclic hydrocarbons, all of which may each be saturated, unsaturated or aromatic,
n denotes an integer from 3 to 64.

5. The cosmetic agent of claim 2, wherein said water-soluble polymer is selected from at least one compound of general formula (PE-2)

T-K-A-K'-T' (PE-2)

in which:
A denotes a polyoxyalkylene chain selected from the group consisting of ethylene oxide units, and the combination of ethylene oxide and propylene oxide units, wherein the polyoxyalkylene chain has a maximum proportion of 50 wt. % of propylene oxide units, relative to the weight of A,
K and K' independently of one another, denote a connectivity selected from a covalent bond or from a molecular fragment having two free valences,
T and T' denote a molecular fragment comprising at least one —$Si(OR)_x(R')_{3-x}$ residue, in which R and R', independently of one another, denote a ($C_1$ to $C_4$) alkyl group and x denotes 1, 2 or 3.

6. The cosmetic agent of claim 2, wherein said at least one water-soluble polymer comprises a solid particle which:
 (i) is surface-modified with polyethers, wherein the polyethers comprise a polyoxyalkylene chain selected from the group consisting of ethylene oxide units, and the combination of ethylene oxide and propylene oxide units, wherein the polyoxyalkylene chain has a maximum proportion of 50 wt. % of propylene oxide units, relative to the weight of the polyoxyalkylene chain,
 (ii) has at least one *—$Si(OR)_x(R')_{3-x}$ residue, in which R and R', independently of one another, denote a ($C_1$ to $C_4$) alkyl group and x denotes 1, 2 or 3.

7. The cosmetic agent of claim 4, wherein A denotes a structural fragment of formula (A1),

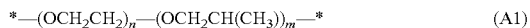 (A1)

in which:
n denotes an integer from 1 to 500,
m denotes an integer from 0 to 500, and
the structural fragment of formula (A1) has a maximum proportion of 50 wt. % of propylene oxide units, relative to the weight of the structural fragment (A1).

8. The cosmetic agent of claim 5, wherein A denotes a structural fragment of formula (A1)

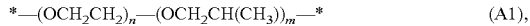 (A1), in which:
n denotes an integer from 1 to 500,
m denotes an integer from 0 to 500, and
the structural fragment of formula (A1) has a maximum proportion of 50 wt. % of propylene oxide units, relative to the weight of the structural fragment (A1).

9. The cosmetic agent of claim 2, wherein K" denotes a covalent bond, an oxy group, an imino group, a ($C_1$ to $C_6$) alkylene group or at least one of the following connectivities (K1) to (K10)

 (K1)

 (K2)

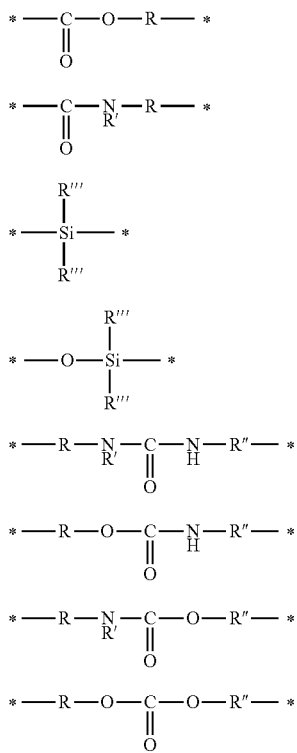

in which

R and R" independently of one another, denote methylene, ethane-1,2-diyl, propane-1,2-diyl, propane-1,3-diyl, butane-1,2-diyl, butane-1,3-diyl, butane-1,4-diyl or phenylene, R' denotes a hydrogen atom or a ($C_1$ to $C_4$) alkyl group, R''' independently of one another, denotes a ($C_1$ to $C_4$) alkyl group or an aryl group.

10. The cosmetic agent of claim 4, wherein the residues K, K' and K", independently of one another, denote a covalent bond, an oxy group, an imino group, a ($C_1$ to $C_6$) alkylene group or at least one of the following connectivities (K1) to (K10)

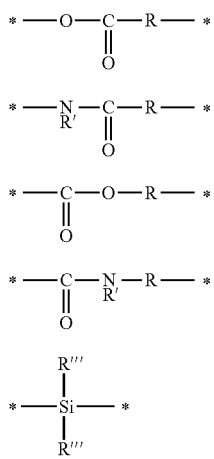

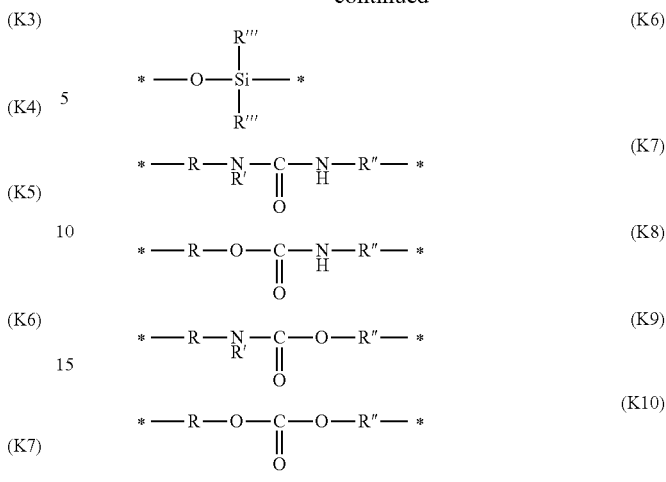

in which:

R and R" independently of one another, denote methylene, ethane-1,2-diyl, propane-1,2-diyl, propane-1,3-diyl, butane-1,2-diyl, butane-1,3-diyl, butane-1,4-diyl or phenylene, R' denotes a hydrogen atom or a ($C_1$ to $C_4$) alkyl group, R''' independently of one another, denotes a ($C_1$ to $C_4$) alkyl group or an aryl group.

11. The cosmetic agent of claim 5, wherein the residues K, K' and K", independently of one another, denote a covalent bond, an oxy group, an imino group, a ($C_1$ to $C_6$) alkylene group or at least one of the following connectivities (K1) to (K10)

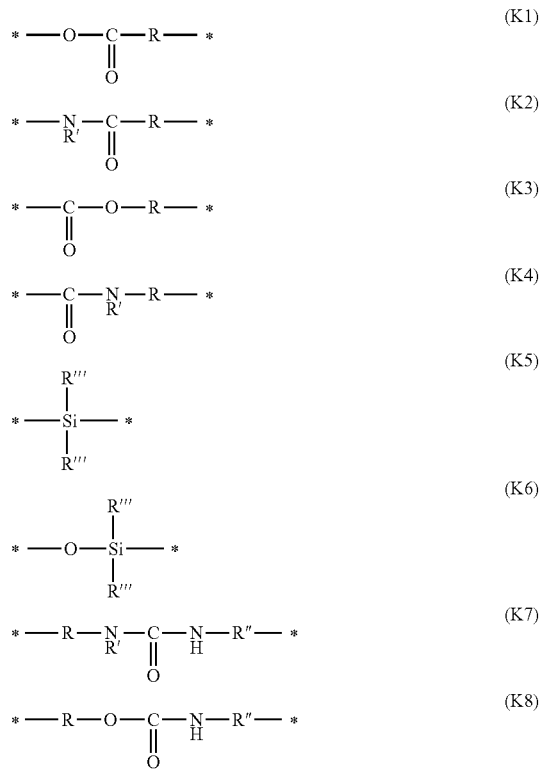

-continued

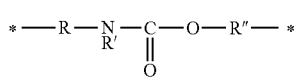
(K9)

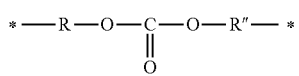
(K10)

in which:

R and R" independently of one another, denote methylene, ethane-1,2-diyl, propane-1,2-diyl, propane-1,3-diyl, butane-1,2-diyl, butane-1,3-diyl, butane-1,4-diyl or phenylene, R' denotes a hydrogen atom or a ($C_1$ to $C_4$) alkyl group, R''' independently of one another, denotes a ($C_1$ to $C_4$) alkyl group or an aryl group.

12. The cosmetic agent of claim 2, wherein said water-soluble polymer of component (a) is included in an amount from 0.01 to 15.0 weight percent (wt. %), relative to the total weight of the agent.

13. The cosmetic agent of claim 2, wherein the at least one polar alkoxysilane of formula (SI) comprises a compound of formula (SI-1)

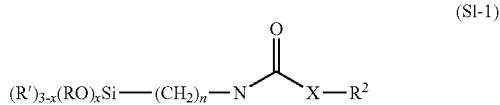
(SI-1)

in which:

R and R' independently of one another, denote a ($C_1$ to $C_4$) alkyl group, x denotes 1, 2 or 3, n denotes 1, 2 or 3, X denotes an oxygen atom or an NH group, $R^2$ denotes a *—$(CH_2)_m$—$NR^3R^4$ group in which m denotes an integer in the range of 2 to 6 (inclusive), $R^3$ and $R^4$, independently of one another, denote ($C_1$ to $C_{20}$) alkyl, ($C_8$ to $C_{20}$) acyloxy ($C_2$ to $C_3$) alkyl, ($C_2$ to $C_{20}$) alkenyl, ($C_8$ to $C_{20}$) alkanamido ($C_2$ to $C_3$) alkyl or aryl ($C_1$ to $C_4$) alkyl.

14. The cosmetic agent of claim 2, wherein said polar alkoxysilane of component (b) is included in an amount from 0.01 to 15.0 wt. %, relative to the total weight of the agent.

15. The cosmetic agent of claim 2, wherein said water-soluble polymer of component (a) and said polar alkoxysilane of component (b) are included in a weight ratio range from 10:1 to 1:10.

16. The cosmetic agent of claim 15, wherein said water-soluble polymer of component (a) and said polar alkoxysilane of component (b) are included in a weight ratio range from 4:1 to 1:4.

17. The cosmetic agent of claim 2, additionally comprising at least one compound selected from organic amines comprising 2 to 20 carbon atoms, carboxylate complex compounds of tin, alkoxide compounds of tin, carboxylate complex compounds of lead, organoaluminum compounds, metal complexes of organic dicarbonyl compounds and metal complexes of organic dicarboxylic acid esters.

18. The cosmetic agent of claim 2, additionally comprising at least one oxidizing agent.

19. The cosmetic agent of claim 18, wherein the at least one oxidizing agent comprises hydrogen peroxide or an addition product thereof.

20. The cosmetic agent of claim 2, wherein the coloring compound comprises at least one oxidation dye precursor of the developer component type.

* * * * *